(12) United States Patent
Kaufman et al.

(10) Patent No.: US 7,439,061 B2
(45) Date of Patent: Oct. 21, 2008

(54) DNA ENCODING THE NOVEL MAMMALIAN PROTEIN, IRE1P

(75) Inventors: Randal J. Kaufman, Ann Arbor, MI (US); Witoon Tirasphon, Ann Arbor, MI (US); Ajith A. Welihinda, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 468 days.

(21) Appl. No.: 10/891,973

(22) Filed: Jul. 14, 2004

(65) Prior Publication Data
US 2005/0059052 A1    Mar. 17, 2005

Related U.S. Application Data

(63) Continuation of application No. 09/357,273, filed on Jul. 20, 1999, now abandoned.

(60) Provisional application No. 60/093,526, filed on Jul. 21, 1998.

(51) Int. Cl.
*C12N 15/85* (2006.01)
*C12N 15/79* (2006.01)
*C12N 15/63* (2006.01)
*C12N 15/52* (2006.01)
*C12N 1/21* (2006.01)

(52) U.S. Cl. .................. 435/325; 435/252.3; 435/320.1; 536/23.2

(58) Field of Classification Search ........................ None
See application file for complete search history.

(56) References Cited

U.S. PATENT DOCUMENTS 4,518,584 A    5/1985    Mark et al.

OTHER PUBLICATIONS

Candau, R. et al., "Identification of human proteins functionally conserved with the yeast putative adaptors ADA2 and GCN5," Mol. Cell. Biol. 16:593-602 (1996).
Cao, X. et al., "Requirement of tyrosine- and serine/threonine kinases in the transcriptional activation of the mammalian grp78/BiP promoter by thapsigargin," J. Biol. Chem. 270:494-502 (1995).
Chang, S.C. et al., "Rat gene encoding the 78-kDa glucose-regulated protein GRP78: its regulatory sequences and the effect of protein glycosylation on its expression," Proc. Natl. Acad. Sci. USA. 84:680-684 (1987).
Chapman, R.E. et al., "Translational attenuation mediated by an mRNA intron," Cur. Biol. 7:850-859 (1997).
Chen, C.A. et al., "Calcium phosphate-mediated gene transfer: a highly efficient transfection system for stably transforming cells with plasmid DNA," BioTechniques 6:632-638 (1988).
Chen, K. et al., "Involvement of p38 mitogen-activated protein kinase signaling pathway in the rapid induction of the 78-kDa glucose-regulated protein in 9L rat brain tumor cells." J.Biol. Chem. 273:749-755 (1998).
Cox, J.S. et al., "Transcriptional induction of genes encoding endoplasmic reticulum resident proteins requires a transmembrane protein kinase," Cell 73:1197-1206 (1993).
Dorner, A.J. et al., "Increased synthesis of secreted proteins induces expression of glucose-regulated proteins in butyrate-treated Chinese hamster ovary cells," J. Biol. Chem. 264:20602-20607 (1989).
Gething et al., "Protein folding in the cell," Nature 355:33-45 (1992).
Gorner, C.J. et al., "Glucose regulated protein induction and cellular resistance to oxidative stress mediated by porphyrin photosensitization," Cancer Res. 51:6574-6579 (1991).
Hanks, S.K. et al., "Protein kinase catalytic domain sequence database: identification of conserved features of primary structure and classification of family members," Methods Enzymol. 200:38-62 (1991).
Hanks, S.K. et al., "Protein kinases 6. The eukaryotic protein kinase superfamily: kinase (catalytic) domain structure and classification," FASEB J. 9:576-596 (1995).
Resendez, E.J. et al., "Identification of highly conserved regulatory domains and protein-binding sites in the promoters of the rat and human genes encoding the stress-inducible 78-kilodalton glucose-regulated protein," Mol Cell. Biol. 8:4579-4584 (1988).
Resendez, E. et al., "Calcium ionophore A23187 as a regulator of gene expression in mammalian cells," J. Cell Biol., Dec. 1986; 103(6 Pt 1):2145-52, J. Cell Biol. 103:2145-2152 (1986).
Rudinger, "Peptide Hormones," (ed. J. A. Parsons) University Park Press, Baltimore, pp. 1-7, 1976.
Sambrook J. et al., Molecular Cloning: A Laboratory Manual, Second Edition, vol. 2, Cold Spring Harbor Laboratory Press, Cold Spring, NY at pp. 8.46-8.47 (1989).
Saragovi, H.U. et al., "Loops and secondary structure mimetics: development and applications in basic science and rational drug design," BioTechnology 10:773-778 (1992).
Shamu, C.E. et al., "Oligomerization and phosphorylation of the Ire1p kinase during intracellular signaling from the endoplasmic reticulum to the nucleus," EMBO J. 15:3028-3039 (1996).
Shen, J. et al., "Coinduction of glucose-regulated proteins and doxorubicin resistance in Chinese hamster cells," Proc. Natl. Acad. Sci. USA 84:3278-3282 (1987).
Sidrauski, K. et al., "The transmembrane kinase Ire1p is a site-specific endonuclease that initiates mRNA splicing in the unfolded protein response," Cell 90:1031-1039 (1997).
Simos, G. et al., "Nuclear pore proteins are involved in the biogenesis of functional tRNA," EMBO J. 15:2270-2284 (1996).
Sugawara, S. et al., "Suppression of stress protein GRP78 induction in tumor B/C10ME eliminates resistance to cell mediated cytotoxicity," Cancer Res. 53:6001-6005 (1993).
Tirasophon, W. et al., Genes Dev., 12:1812-1824 in Current Protocols in Molecular Biology, John Wiley & Sons, NY, 6.31-6.3.6 (1998).

(Continued)

Primary Examiner—Robert C Hayes
(74) Attorney, Agent, or Firm—DeAnn F. Smith; Foley Hoag LLP

(57) ABSTRACT

A novel polynucleotide encoding a mammalian bifunctional protein kinase\endoribonuclease referred to herein as hIre1p, is provided. hIre1p is expressed in the endoplasmic reticulum (ER) and upregulates the transcription of genes encoding ER protein chaperones, such as, but not limited to, glucose-related proteins (GRP's). Therapeutic, diagnostic and research methods employing the polynucleotide and protein are also provided.

9 Claims, 12 Drawing Sheets

OTHER PUBLICATIONS

Trotta C.R et al., "The yeast tRNA splicing endonuclease:a tetrameric enzyme with two active site subunits homologous to the archaeal tRNA endonucleases," Cell 89:849-858 (1997).

Welihinda, A.A. et al., "The unfolded protein response pathway in *Saccharomyces cerevisiae*. Oligomerization and trans-phosphorylation of Ire1p (Em1p) are required for kinase activation," J. Biol. Chem. 271:18181-18187 (1996).

Welihinda, A.A. et al., "Gene induction in response to unfolded protein in the endoplasmic reticulum is mediated through Ire1 p kinase interaction with a transcriptional coactivator complex containing Ada5p," Proc. Natl. Acad. Sci. USA. 94:4289-4294 (1997).

Zhou A. et al., "Expression cloning of 2-5A-dependent RNAase: a uniquely regulated mediator of interferon action," Cell 72:753-765 (1993).

Hartl, F.U., "Molecular chaperones in cellular protein folding," Nature 381:571-579 (1996).

Hughes, C.S. et al., "Resistance to etoposide induced by three glucose-regulated stresses in Chinese hamster ovary cells," Cancer Res. 49:4452-4454 (1989).

Kaufman, "Selection and coamplification of heterologous genes in mammalian cells," Methods in Enzymology 185:537-566 (1990).

Kaufman et al., "Improved vectors for stable expression of foreign genes in mammalian cells by use of the untranslated leader sequence from EMC virus," Nucleic Acids Res. 19:4485-4490 (1991).

Kaufman, R.J., "Overview of vector design for mammalian gene expression.," Methods Mol. Biol. 62:287-300 (1997).

Kawahara, T. et al., "Endoplasmic reticulum stress-induced mRNA splicing permits synthesis of transcription factor Hac1p/Ern4p that activates the unfolded protein response," Mol. Biol. Cell 8:1845-1862 (1997)-.

Kawahara; T: et-al; "Unconventional-splicing of HAC1/ERN4 mRNA required for the unfolded protein response. Sequence-specific and non-sequential cleavage of the splice sites," J. Biol. Chem. 273:1802-1807 (1998).

Kozak, M., "An analysis of 5'-noncoding sequences from 699 vertebrate messenger RNAs," Nucl. Acids Res. 15:8125-8248 (1987).

Kozutsumi, Y. et al., "The presence of malfolded proteins in the endoplasmic reticulum signals the induction of glucose-regulated proteins," Nature 332:462-464 (1988).

Lee, AS., "Coordinated regulation of a set of genes by glucose and calcium ionophores in mammalian cells," TIBS, 12:20-23 (1987).

Li, X.A. et al., "Competitive inhibition of a set of endoplasmic reticulum protein genes (GRP78, GRP94, and ERp72) retards cell growth and lowers viability after ionophore treatment," Mol. Cell. Biol. 11:3446-3453 (1991).

Li, L J. et al., "Establishment of a Chinese hamster ovary cell line that expresses grp78 antisense transcripts and suppresses A23187 induction of both GRP78 and GRP94," J. Cell Physiol. 153:575-582 (1992).

Mahajan, R. et al., "A small ubiquitin-related polypeptide involved in targeting RanGAP1 to nuclear pore complex protein RanBP2," Cell 88:97-107 (1997).

Maniatis, T., et al., Molecular Cloning: A Laboratory Manual, Cold Spring Harbor Laboratory Press, Cold Spring NY, at pp. 387-389, (1982).

McDowell, R.S. et al., "Structural studies of potent constraint RGD peptides," J. Amer. Chem. Soc. 114:9245-9253 (1992).

Mori, K. et al., "A 22 by cis-acting element is necessary and sufficient for the induction of the yeast KAR2 (BIP) gene by unfolded proteins," EMBO J. 11:2583-2593 (1992).

Mori, K. et al., "A transmembrane protein with a cdc2+/CDC28-related kinase activity is required for signaling from the ER to the nucleus," Cell 74:743-756 (1993).

Mori, K. et al., "Signalling from endoplasmic reticulum to nucleus: transcription factor with a basic-leucine zipper motif is required for the unfolded protein-response pathway," Genes to Cells. 1:803-817 (1996).

Morris, J.A. et al., "Immunoglobulin binding protein (BiP) function is required to protect cells from endoplasmic reticulum stress but is not required for the selection of secretion proteins," J. Biol. Chem. 272:4327-4334 (1997).

Nielsen, H et al., "Identification-of prokaryotic and eukaryotic signal peptides and prediction of their cleavage sites," Protein Eng. 10:1-6 (1997).

Nikawa, J. et al., "IRE1 encodes a putative protein kinase containing a membrane-spanning domain and is required for inositol phototrophy in *Saccharomyces cerevisiae*," Mol. Microbiol. 6:1441-1446 (1992).

Paterson et al., "Microinjection of epitope-tagged Rho family cDNAs and analysis by immunolabeling," Meth. Enzymol. 256:162-173 (1995).

```
H.s.           VPARRLLLLLLLPGLGIFGSTSTVTLPETLHVSTIDGSLHAVSKRTGSIKWTLKE    58
C.e.  MRATFHLFTFIFLLLFSSVECKSTPGFRNDHESIGDDEEKTSSTILVSTIDGRLRALDSETGEIKWTLQE    70

H.s.  DPVLGVPTHVEEPA-FLPDPNDGSLYILGSKNNEGLIKLPFTIPELVQASPQSSDGILYMGKKQDIWLV   127
C.e.  EPVLRSPSAVKQGFTFLPNELDGSLYVML--KNSS-LKKLPFNIPQLVHASPQRGNDGILYAGSKRDVWEG  137

H.s.  IDLLTGEKQC---------------TLSSAFADSECPST--SLEYLGRTEYTTEMYDIKTRELRWNATY   179
C.e.  IDPKTGLKVEYILLNISDKILFLQVETLSSASADRECPANQKQTTELGRTEYRVSMEDEKNRGKTWNATE   207

H.s.  FDYAA-SLPEDEGDYKMSHEVSNGDGLVVIVDSESCDMLWICNYASPVVAFYMWQREGLRKVMHINVAVE   248
C.e.  NDYSAHLLPE-VNTHPFKHHASSSHGYKLTFDRELGEMRWECDLKQPVVALYLRDEGLHKEPFEVMGKE   276

H.s.  TLRYLTFMSGEVGRITKWKYPF---PKETEAKSKLTHTLVGKYSTSLYASPSMV-HEGVAVVPGSTLP   314
C.e.  TMENVAKNIFTVDQWPTVLGVNAADPQITLSLTNGFFHALEVGSSSFGLYAIEALVDHQTFTYSPRLLGPP  346

H.s.  LLEGPQTDGVTIGDKGECVITPSTDVEFDPGLKSKNKLNYLRNYWLLIGHHZTPL-SASTKMLEREPNNL   383
C.e.  LLEGPAPIALTEMEKEDYLPPRRPILRNIPPSITHK---TSDGEXLLIGYHDPMMEMATIIPTRYEVPG   413

H.s.  PKHRENVIPADSEKKSFEEVINLVDQTSENAPTTMSRDVEEKPAHAPARPEAPYDSMLKDMATIILSTFL   453
C.e.  PHKAIGSTIERPPPQLLGPVEPQKHEDTSFILLLMNNHPIPFYATLVTMFALLLTVIWQCGRQWDQQKST   483
                                                    I
H.s.  LIGWVAFITTYPLSMHQQQQLQHQQFQKELEKIGLKQQGQQLPFHPPGDTAQDGELLDTSGPYSESSGT   523
C.e.  SRMDSFEIMNNEGESRSAQTSKQSNRGSFGWANRKLEIPEGW------------------------   525
                  II
H.s.  SSPSTSPRASNHSLCSGSSASKAGSSPSLEQDDGDEETSVVTVGKISFCPKDVLGHGAEGTILVRGMFDN   593
C.e.  ----------------------------------------MAVGSKLMYSPSDILGTGCEGTMVYRGTFDG   556
S.c.                                           LVVSCKILGYGSSGTMVVSQGSFDG   696
                  *                                      *
H.s.  RDVAVKRIEPECFSEADREVCLIRESDEHPNVIRYFCTEKDRQFQYIALELQAATLQRYVEQKDFAHLGL   663
C.e.  REVAVKRVVSEFVKFAHREADLLRESDEHPNVIRYFCTEKDSQFRYIALELCTASLNDYVEQKEVQQNVT   626
S.c.  RPVAVKRMIIDFCDIALMEIKLLIESDDHPNVIRYFCSETTDRFLYHALELQNLNLQLIVESKNVSDENL   766
              *                          *           *

H.s.  ------EPITLLQQTTSGLAHLHSLNIVHRDLKPHNILSMPN--------AHGKIKAMISDFGLCKKIA   719
C.e.  IALRD-----IMKQATDGLAHLHASKIVHRDLKPQNMLLMAS--------QRGEMRAVISDFGLCKRVQ   693
S.c.  KLQKEYNPISLLERQIASGVAHLHSLKIIHRDLKPQNVLVSTSSRFTADQQTGAENLKILISDFGLCKKLD   836
                                                                        *

H.s.  VGRHSFSRR--SGVPGTEGWIAPEMLSEDCKEN----------------------PLYTVDIFS   759
C.e.  PGKNSISRGIASGLAGTDGWIAPEMLISAST---------------------------SYPVDIFS   722
S.c.  SGQSSFRTNLNNPS-GTSGWRAPEILEESNNLQCQVETEHSSSRHTVVSSDSFYDPFTKRRLRSIDIFS   905
          *                                                                *

H.s.  AGCVFYYVVSEGSHPFGKSLQRQANILLGACSLDCLHPEKH--EDVIARELIEKMEAMDPQKRPSANDVL   827
C.e.  IGCBFYYVMHSGTHPFGKSLHRQANIMNGEYTINKLADLDD---WSLADDLISSMINVEPLHRLTADAVI   789
S.c.  MGCVFYYTLSKGKHPFGDKYSRESNIHRGIFSLDEMKCLHDRSLIAEATDLISQMEDHPLKRPTAMKVL   975

H.s.  KHPFFWSLEKQLQEFQDVSDRIE---KESLDGPEVKQLERGGRAVVKMDWRENITDPLQTDLRKERIYKG  894
C.e.  NHPFFWTSEKRLAYFSDVSDRME---KEDNSPVVRRIETDARIVCGGWREKICDALKEDLRKERITYKS   856
S.c.  RHPIFWPKSKKLELLLKVSDRIEIENEDPPSALEMKFDAGSDFVLPSGDWTVKFDKTFMDLERTRKYHS   1045

H.s.  GSVRDLLRAMRNKKHHFRGLPAERETLGTLPDDFVCYFTSRFPHLIAHTYRAMELCSHERLFQPYEFHE   964
C.e.  FSVRDLLRAMRNKKHHYRELPEDGREGSIGDIPDQFFLHYFTSRFPRLLILHVYKATEYCSGEAVFKRYWSDD  926
S.c.  SKEMDLLRAIRNKYHFEMDLPEDIAELMGPMPDGFYDYFTKRFPNLLIIGVYMIVKENLSEDQILREELYS   1115

H.s.  PPEPQPPVTPRAL                                                       977
C.e.  VRARMYPIVEEEERVRKKIKEEMANEVWARAPKPVEQRTPLKLDKRNIKKKSNPNTD           983
```

*Fig. 1C*

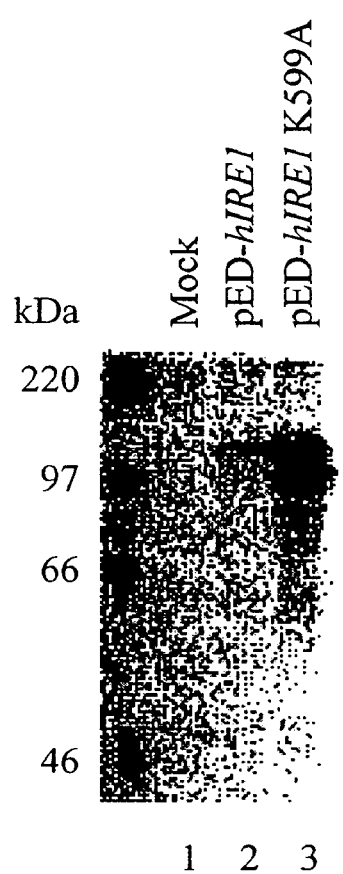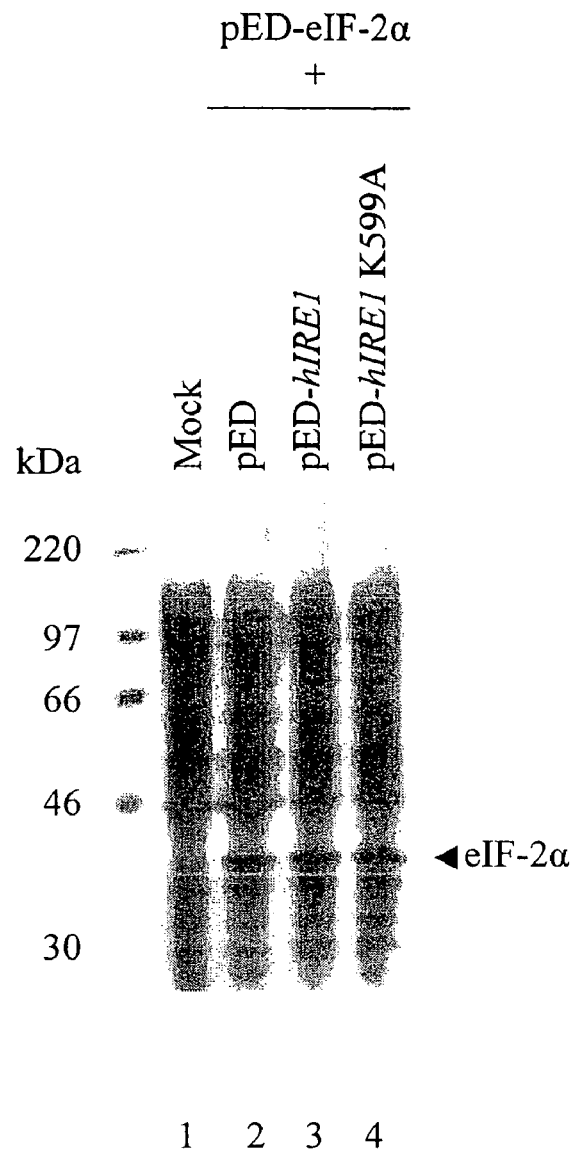
Fig. 3A
Fig. 3B

```
   1 ccggctcgac ggctcggtca ccgcctcgct gtcgtcgcgg cgccccggc cgtcctctgt
  61 ccgtaccgcc cccggagcca gggccgagtc ctcgccatgc cggcccggcg gctgctgctg
 121 ctgctgacgc tgctgctgcc cggcctcggg attttggaa gtaccagcac agtgacgctt
 181 cctgaaacct tgttgtttgt gtcaacgctg gatggaagtt tgcatgctgt cagcaagagg
 241 acaggctcaa tcaaatggac tttaaaagaa gatccagtcc tgcaggtccc aacacatgtg
 301 gaagagcctg cctttctccc agatcctaat gatggcagcc tgtatacgct tggaagcaag
 361 aataatgaag gcctgacgaa acttcctttt accatcccag aattggtgca ggcatcccca
 421 tgccgaagtt cagatggaat cctctacatg ggtaaaaagc aggacatctg gtatgttatt
 481 gacctcctga ccggagagaa gcagcagact ttgtcatcgg cctttgcaga tagtctctgc
 541 ccatcaacct ctcttctgta tcttgggcga acagaataca ccatcaccat gtacgacacc
 601 aaaacccgag agctccggtg gaatgccacc tactttgact atgcggcctc actgcctgag
 661 gacgaagggg actacaagat gtcccacttt gtgtccaatg gtgatgggct ggtggtgact
 721 gtggacagtg aatctgggga cgtcctgtgg atccaaaact acgcctcccc tgtggtggcc
 781 ttttatgtct ggcagcggga gggtctgagg aaggtgatgc acatcaatgt cgctgtggag
 841 accctgcgct atctgacctt catgtctggg gaggtggggc gcatcacaaa gtggaagtac
 901 ccgttcccca aggagacaga ggccaagagc aagctgacgc ccactctgta tgttgggaaa
 961 tactctacca gcctctatgc ctctccctca atggtacacg aggggttgc tgtcgtgccc
1021 cgcggcagca cacttccttt gctggaaggg cccagactg atggcgtcac catcggggac
1081 aaggggagt gtgtgatcac gcccagcacg gacgtcaagt tgatcccgg actcaaaagc
1141 aagaacaagc tcaactactt gaggaattac tggcttctga taggacacca tgaaacccca
1201 ctgtctgcgt ctaccaagat gctggagaga tttcccaaca atctacccaa acatcgggaa
1261 aatgtgattc ctgctgattc agagaaaaag agctttgagg aagttatcaa cctggttgac
1321 cagacttcag aaaacgcacc taccaccgtg tctcgggatg tggaggagaa gcccgcccat
1381 gccccctgcc ggcccgaggc cccgtggac tccatgctta aggacatggc taccatcatc
1441 ctgagcacct tcctgctgat tggctgggtg gccttcatca tcacctatcc cctgagcatg
1501 catcagcagc agcagctcca gcaccagcag ttccagaagg aactggagaa gatccagctc
1561 ctgcagcagc agcagcagca gctgcccttc cacccacctg gagacacggc tcaggacggc
1621 gagctcctgg acacgtctgg cccgtactca gagagctcgg gcaccagcag ccccagcacg
1681 tccccaggg cctccaacca ctcgctctgc tccggcagct ctgcctccaa ggctggcagc
1741 agcccctccc tggaacaaga cgatggagat gaggaaacca gcgtggtgat agttgggaaa
1801 atttccttct gtccaaggat gtcctgggc catggagctg agggcacaat tgtgtaccgg
1861 ggcatgttg acaaccgcga cgtggccgtg aagaggatcc tccccgagtg ttttagcttc
1921 gcagaccgtg aggtccagct gttgcgagaa tcggatgagc acccgaacgt gatccgctac
1981 ttctgcacgg agaaggaccg gcaattccag tacattgcca tcgagctgtg tgcagccacc
2041 ctgcaagagt atgtggagca aaggactttt gcgcatctcg gcctggagcc catcaccttg
2101 ctgcagcaga ccacctcggg cctggcccac ctccactccc tcaacatcgt tcacagagac
2161 ctaaagccac acaacatcct catatccatg cccaatgcac acggcaagat caaggccatg
2221 atctccgact ttggcctctg caagaagctg gcagtgggca gacacagttt cagccgccga
2281 tctggggtgc ctggcacaga aggctggatc gctccagaga tgctgagcga agactgtaag
2341 gagaacccta cctacacggt ggacatcttt tctgcaggct gcgtcttta ctacgtggtc
2401 tctgagggca gccacccttt tggcaagtcc ctgcagcggc aggccaacat cctcctgggt
2461 gcctgcagcc ttgactgctt gcacccagag aagcacgaag acgtcattgc acgagaattg
2521 atagagaaga tgattgcgat ggatcctcag aaacgcccct cagcgaacga cgtgctcaaa
2581 caccgttct tctggagcct agagaagcag ctccagttct ccaggacgt gagcgacaga
2641 atagaaaagg aatccctgga tggcccgatc gtgaagcagt tagagagagg cgggagagcc
2701 gtggtgaaga tggactggcg ggagaacatc actgacccc tccagacaga cctgcgtaaa
2761 tcaggacct ataaaggtgg ttctgtcaga gatctcctcc gagccatgag aaataagaag
2821 caccactacc gggagctgcc tgcagaggtg cgggagacgc tggggaccct cccgacgac
2881 ttcgtgtgct acttcacgtc tcgcttcccc acctcctcg cacacaccta ccgggccatg
2941 gagctgtgca gccacgagag actcttccag ccctactact tccacgagcc cccagagccc
```

*Fig. 8A*

```
3001 cagcccccag tgactccaga cgccctctga gcgagggcgg cccctctgtt ctggtggccc
3061 cagctgtgac tgagggcctg gtcaccacaa ttagagcttg atgcctcccg gctttgcagg
3121 gagaccaggc ttcccaaacc aagtgccttg agctgcctgc tctgcagccc acagaggaca
3181 gtgctgaccc caggaagtgg gagaagtggc ccctcgtgac ctacagggaa ctgggaagat
3241 gctggcccca aaagccttac ggtcatgatg tctgcaaagg agggcctcag agacagcgcg
3301 agtagcaccc ccagccatct actggataaa cttgcttcag actttttaaa ttcctgctta
3361 atgtcagtct acaggccttt caggaaggga gaggagggaa tcgtacattt tgcttgcgtg
3421 ctgggacagc taggctgaga tgcaccaagt acagccttca ctggagaccg gaattgagag
3481 gtggggatg ctgaggaggg ggaggacgga gttcagaggg tgtcgtcctg cagtatgaga
3541 tttctcattg atcacagatg tgcccagagt agcccaggtc actgttaact agtgtttctg
3601 cagaggcagc aggagccagc ccggaattc
```

*Fig. 8B*

```
MPARRLLLLLTLLLPGLGIFGSTSTVTLPETLLFVSTLDGSLHAVSKRTGSIKWTLKEDP    60
VLQVPTHVEEPAFLPDPNDGSLYTLGSKNNEGLTKLPFTIPELVQASPCRSSDGILYMGK   120
KQDIWYVIDLLTGEKQQTLSSAFADSLCPSTSLLYLGRTEYTITMYDTKTRELRWNATYF   180
DYAASLPEDEGDYKMSHFVSNGDGLVVTVDSESGDVLWIQNYASPVVAFYVWQREGLRKV   240
MHINVAVETLRYLTFMSGEVGRITKWKYPFPKETEAKSKLTPTLYVGKYSTSLYASPSMV   300
HEGVAVVPRGSTLPLLEGPQTDGVTIGDKGECVITPSTDVKFDPGLKSKNKLNYLRNYWL   360
LIGHHETPLSASTKMLERFPNNLPKHRENVIPADSEKKSFEEVINLVDQTSENAPTTVSR   420
DVEEKPAHAPARPEAPVDSMLKDMATIILSTFLLIGWVAFIITYPLSMHQQQQLQHQQFQ   480
KELEKIQLLQQQQQQLPFHPPGDTAQDGELLDTSGPYSESSGTSSPSTSPRASNHSLCSG   540
SSASKAGSSPSLEQDDGDEETSVVIVGKISFCPKDVLGHGAEGTIVYRGMFDNRDVAVKR   600
ILPECFSFADREVQLLRESDEHPNVIRYFCTEKDRQFQYIAIELCAATLQEYVEQKDFAH   660
LGLEPITLLQQTTSGLAHLHSLNIVHRDLKPHNILISMPNAHGKIKAMISDFGLCKKLAV   720
GRHSFSRRSGVPGTEGWIAPEMLSEDCKENPTYTVDIFSAGCVFYYVVSEGSHPFGKSLQ   780
RQANILLGACSLDCLHPEKHEDVIARELIEKMIAMDPQKRPSANDVLKHPFFWSLEKQLQ   840
FFQDVSDRIEKESLDGPIVKQLERGGRAVVKMDWRENITDPLQTDLRKFRTYKGGSVRDL   900
LRAMRNKKHHYRELPAEVRETLGTLPDDFVCYFTSRFPHLLAHTYRAMELCSHERLFQPY   960
YFHEPPEPQPPVTPDAL                                              977
```

*Fig. 9*

SEQUENCE LISTING

```
<160> NUMBER OF SEQ ID NOS: 13

<210> SEQ ID NO 1
<211> LENGTH: 3629
<212> TYPE: DNA
<213> ORGANISM: Homo sapiens
<220> FEATURE:
<221> NAME/KEY: CDS
<222> LOCATION: (97)..(3027)

<400> SEQUENCE: 1
ccggctcgac ggctcggtca ccgcctcgct gtcgtcgcgg cgccccggc cgtcctctgt     60 ccgtaccgcc cccggagcca gggccgagtc ctcgcc atg ccg gcc cgg cgg ctg    114
                                        Met Pro Ala Arg Arg Leu
                                         1               5 ctg ctg ctg ctg acg ctg ctg ctg ccc ggc ctc ggg att ttt gga agt    162
Leu Leu Leu Leu Thr Leu Leu Leu Pro Gly Leu Gly Ile Phe Gly Ser
             10                  15                  20 acc agc aca gtg acg ctt cct gaa acc ttg ttg ttt gtg tca acg ctg    210
Thr Ser Thr Val Thr Leu Pro Glu Thr Leu Leu Phe Val Ser Thr Leu
         25                  30                  35 gat gga agt ttg cat gct gtc agc aag agg aca ggc tca atc aaa tgg    258
Asp Gly Ser Leu His Ala Val Ser Lys Arg Thr Gly Ser Ile Lys Trp
     40                  45                  50 act tta aaa gaa gat cca gtc ctg cag gtc cca aca cat gtg gaa gag    306
Thr Leu Lys Glu Asp Pro Val Leu Gln Val Pro Thr His Val Glu Glu
 55                  60                  65                  70 cct gcc ttt ctc cca gat cct aat gat ggc agc ctg tat acg ctt gga    354
Pro Ala Phe Leu Pro Asp Pro Asn Asp Gly Ser Leu Tyr Thr Leu Gly
                 75                  80                  85 agc aag aat aat gaa ggc ctg acg aaa ctt cct ttt acc atc cca gaa    402
Ser Lys Asn Asn Glu Gly Leu Thr Lys Leu Pro Phe Thr Ile Pro Glu
             90                  95                 100
```

-continued

| | | |
|---|---|---|
| ttg gtg cag gca tcc cca tgc cga agt tca gat gga atc ctc tac atg<br>Leu Val Gln Ala Ser Pro Cys Arg Ser Ser Asp Gly Ile Leu Tyr Met<br>     105                    110                    115 | 450 | |
| ggt aaa aag cag gac atc tgg tat gtt att gac ctc ctg acc gga gag<br>Gly Lys Lys Gln Asp Ile Trp Tyr Val Ile Asp Leu Leu Thr Gly Glu<br>120                    125                    130 | 498 | |
| aag cag cag act ttg tca tcg gcc ttt gca gat agt ctc tgc cca tca<br>Lys Gln Gln Thr Leu Ser Ser Ala Phe Ala Asp Ser Leu Cys Pro Ser<br>135                    140                    145                    150 | 546 | |
| acc tct ctt ctg tat ctt ggg cga aca gaa tac acc atc acc atg tac<br>Thr Ser Leu Leu Tyr Leu Gly Arg Thr Glu Tyr Thr Ile Thr Met Tyr<br>                    155                    160                    165 | 594 | |
| gac acc aaa acc cga gag ctc cgg tgg aat gcc acc tac ttt gac tat<br>Asp Thr Lys Thr Arg Glu Leu Arg Trp Asn Ala Thr Tyr Phe Asp Tyr<br>                170                    175                    180 | 642 | |
| gcg gcc tca ctg cct gag gac gaa ggg gac tac aag atg tcc cac ttt<br>Ala Ala Ser Leu Pro Glu Asp Glu Gly Asp Tyr Lys Met Ser His Phe<br>                    185                    190                    195 | 690 | |
| gtg tcc aat ggt gat ggg ctg gtg gtg act gtg gac agt gaa tct ggg<br>Val Ser Asn Gly Asp Gly Leu Val Val Thr Val Asp Ser Glu Ser Gly<br>200                    205                    210 | 738 | |
| gac gtc ctg tgg atc caa aac tac gcc tcc cct gtg gtg gcc ttt tat<br>Asp Val Leu Trp Ile Gln Asn Tyr Ala Ser Pro Val Val Ala Phe Tyr<br>215                    220                    225                    230 | 786 | |
| gtc tgg cag cgg gag ggt ctg agg aag gtg atg cac atc aat gtc gct<br>Val Trp Gln Arg Glu Gly Leu Arg Lys Val Met His Ile Asn Val Ala<br>                    235                    240                    245 | 834 | |
| gtg gag acc ctg cgc tat ctg acc ttc atg tct ggg gag gtg ggg cgc<br>Val Glu Thr Leu Arg Tyr Leu Thr Phe Met Ser Gly Glu Val Gly Arg<br>                250                    255                    260 | 882 | |
| atc aca aag tgg aag tac ccg ttc ccc aag gag aca gag gcc aag agc<br>Ile Thr Lys Trp Lys Tyr Pro Phe Pro Lys Glu Thr Glu Ala Lys Ser<br>                265                    270                    275 | 930 | |
| aag ctg acg ccc act ctg tat gtt ggg aaa tac tct acc agc ctc tat<br>Lys Leu Thr Pro Thr Leu Tyr Val Gly Lys Tyr Ser Thr Ser Leu Tyr<br>280                      285                    290 | 978 | |
| gcc tct ccc tca atg gta cac gag ggg gtt gct gtc gtg ccc cgc ggc<br>Ala Ser Pro Ser Met Val His Glu Gly Val Ala Val Val Pro Arg Gly<br>295                    300                    305                    310 | 1026 | |
| agc aca ctt cct ttg ctg gaa ggg ccc cag act gat ggc gtc acc atc<br>Ser Thr Leu Pro Leu Leu Glu Gly Pro Gln Thr Asp Gly Val Thr Ile<br>                315                    320                    325 | 1074 | |
| ggg gac aag ggg gag tgt gtg atc acg ccc agc acg gac gtc aag ttt<br>Gly Asp Lys Gly Glu Cys Val Ile Thr Pro Ser Thr Asp Val Lys Phe<br>                330                    335                    340 | 1122 | |
| gat ccc gga ctc aaa agc aag aac aag ctc aac tac ttg agg aat tac<br>Asp Pro Gly Leu Lys Ser Lys Asn Lys Leu Asn Tyr Leu Arg Asn Tyr<br>                    345                    350                    355 | 1170 | |
| tgg ctt ctg ata gga cac cat gaa acc cca ctg tct gcg tct acc aag<br>Trp Leu Leu Ile Gly His His Glu Thr Pro Leu Ser Ala Ser Thr Lys<br>360                    365                    370 | 1218 | |
| atg ctg gag aga ttt ccc aac aat cta ccc aaa cat cgg gaa aat gtg<br>Met Leu Glu Arg Phe Pro Asn Asn Leu Pro Lys His Arg Glu Asn Val<br>375                    380                    385                    390 | 1266 | |
| att cct gct gat tca gag aaa aag agc ttt gag gaa gtt atc aac ctg<br>Ile Pro Ala Asp Ser Glu Lys Lys Ser Phe Glu Glu Val Ile Asn Leu<br>                    395                    400                    405 | 1314 | |
| gtt gac cag act tca gaa aac gca cct acc acc gtg tct cgg gat gtg<br>Val Asp Gln Thr Ser Glu Asn Ala Pro Thr Thr Val Ser Arg Asp Val | 1362 | |

-continued

```
                    410                 415                 420
gag gag aag ccc gcc cat gcc cct gcc cgg ccc gag gcc ccc gtg gac    1410
Glu Glu Lys Pro Ala His Ala Pro Ala Arg Pro Glu Ala Pro Val Asp
            425                 430                 435 tcc atg ctt aag gac atg gct acc atc atc ctg agc acc ttc ctg ctg    1458
Ser Met Leu Lys Asp Met Ala Thr Ile Ile Leu Ser Thr Phe Leu Leu
440                 445                 450 att ggc tgg gtg gcc ttc atc atc acc tat ccc ctg agc atg cat cag    1506
Ile Gly Trp Val Ala Phe Ile Ile Thr Tyr Pro Leu Ser Met His Gln
455                 460                 465                 470 cag cag cag ctc cag cac cag cag ttc cag aag gaa ctg gag aag atc    1554
Gln Gln Gln Leu Gln His Gln Gln Phe Gln Lys Glu Leu Glu Lys Ile
                475                 480                 485 cag ctc ctg cag cag cag cag cag ctg ccc ttc cac cca cct gga        1602
Gln Leu Leu Gln Gln Gln Gln Gln Leu Pro Phe His Pro Pro Gly
            490                 495                 500 gac acg gct cag gac ggc gag ctc ctg gac acg tct ggc ccg tac tca    1650
Asp Thr Ala Gln Asp Gly Glu Leu Leu Asp Thr Ser Gly Pro Tyr Ser
            505                 510                 515 gag agc tcg ggc acc agc agc ccc agc acg tcc ccc agg gcc tcc aac    1698
Glu Ser Ser Gly Thr Ser Ser Pro Ser Thr Ser Pro Arg Ala Ser Asn
520                 525                 530 cac tcg ctc tgc tcc ggc agc tct gcc tcc aag gct ggc agc agc ccc    1746
His Ser Leu Cys Ser Gly Ser Ser Ala Ser Lys Ala Gly Ser Ser Pro
535                 540                 545                 550 tcc ctg gaa caa gac gat gga gat gag gaa acc agc gtg gtg ata gtt    1794
Ser Leu Glu Gln Asp Asp Gly Asp Glu Glu Thr Ser Val Val Ile Val
                555                 560                 565 ggg aaa att tcc ttc tgt ccc aag gat gtc ctg ggc cat gga gct gag    1842
Gly Lys Ile Ser Phe Cys Pro Lys Asp Val Leu Gly His Gly Ala Glu
                570                 575                 580 ggc aca att gtg tac cgg ggc atg ttt gac aac cgc gac gtg gcc gtg    1890
Gly Thr Ile Val Tyr Arg Gly Met Phe Asp Asn Arg Asp Val Ala Val
            585                 590                 595 aag agg atc ctc ccc gag tgt ttt agc ttc gca gac cgt gag gtc cag    1938
Lys Arg Ile Leu Pro Glu Cys Phe Ser Phe Ala Asp Arg Glu Val Gln
600                 605                 610 ctg ttg cga gaa tcg gat gag cac ccg aac gtg atc cgc tac ttc tgc    1986
Leu Leu Arg Glu Ser Asp Glu His Pro Asn Val Ile Arg Tyr Phe Cys
615                 620                 625                 630 acg gag aag gac cgg caa ttc cag tac att gcc atc gag ctg tgt gca    2034
Thr Glu Lys Asp Arg Gln Phe Gln Tyr Ile Ala Ile Glu Leu Cys Ala
                635                 640                 645 gcc acc ctg caa gag tat gtg gag cag aag gac ttt gcg cat ctc ggc    2082
Ala Thr Leu Gln Glu Tyr Val Glu Gln Lys Asp Phe Ala His Leu Gly
            650                 655                 660 ctg gag ccc atc acc ttg ctg cag cag acc acc tcg ggc ctg gcc cac    2130
Leu Glu Pro Ile Thr Leu Leu Gln Gln Thr Thr Ser Gly Leu Ala His
            665                 670                 675 ctc cac tcc ctc aac atc gtt cac aga gac cta aag cca cac aac atc    2178
Leu His Ser Leu Asn Ile Val His Arg Asp Leu Lys Pro His Asn Ile
680                 685                 690 ctc ata tcc atg ccc aat gca cac ggc aag atc aag gcc atg atc tcc    2226
Leu Ile Ser Met Pro Asn Ala His Gly Lys Ile Lys Ala Met Ile Ser
695                 700                 705                 710 gac ttt ggc ctc tgc aag aag ctg gca gtg ggc aga cac agt ttc agc    2274
Asp Phe Gly Leu Cys Lys Lys Leu Ala Val Gly Arg His Ser Phe Ser
            715                 720                 725 cgc cga tct ggg gtg cct ggc aca gaa ggc tgg atc gct cca gag atg    2322
```

```
                Arg Arg Ser Gly Val Pro Gly Thr Glu Gly Trp Ile Ala Pro Glu Met
                            730                 735                 740 ctg agc gaa gac tgt aag gag aac cct acc tac acg gtg gac atc ttt          2370
Leu Ser Glu Asp Cys Lys Glu Asn Pro Thr Tyr Thr Val Asp Ile Phe
            745                 750                 755 tct gca ggc tgc gtc ttt tac tac gtg gtc tct gag ggc agc cac cct          2418
Ser Ala Gly Cys Val Phe Tyr Tyr Val Val Ser Glu Gly Ser His Pro
            760                 765                 770 ttt ggc aag tcc ctg cag cgg cag gcc aac atc ctc ctg ggt gcc tgc          2466
Phe Gly Lys Ser Leu Gln Arg Gln Ala Asn Ile Leu Leu Gly Ala Cys
775                 780                 785                 790 agc ctt gac tgc ttg cac cca gag aag cac gaa gac gtc att gca cga          2514
Ser Leu Asp Cys Leu His Pro Glu Lys His Glu Asp Val Ile Ala Arg
                795                 800                 805 gaa ttg ata gag aag atg att gcg atg gat cct cag aaa cgc ccc tca          2562
Glu Leu Ile Glu Lys Met Ile Ala Met Asp Pro Gln Lys Arg Pro Ser
            810                 815                 820 gcg aac gac gtg ctc aaa cac ccg ttc ttc tgg agc cta gag aag cag          2610
Ala Asn Asp Val Leu Lys His Pro Phe Phe Trp Ser Leu Glu Lys Gln
            825                 830                 835 ctc cag ttc ttc cag gac gtg agc gac aga ata gaa aag gaa tcc ctg          2658
Leu Gln Phe Phe Gln Asp Val Ser Asp Arg Ile Glu Lys Glu Ser Leu
            840                 845                 850 gat ggc ccg atc gtg aag cag tta gag aga ggc ggg aga gcc gtg gtg          2706
Asp Gly Pro Ile Val Lys Gln Leu Glu Arg Gly Gly Arg Ala Val Val
855                 860                 865                 870 aag atg gac tgg cgg gag aac atc act gac ccc ctc cag aca gac ctg          2754
Lys Met Asp Trp Arg Glu Asn Ile Thr Asp Pro Leu Gln Thr Asp Leu
                875                 880                 885 cgt aaa ttc agg acc tat aaa ggt ggt tct gtc aga gat ctc ctc cga          2802
Arg Lys Phe Arg Thr Tyr Lys Gly Gly Ser Val Arg Asp Leu Leu Arg
            890                 895                 900 gcc atg aga aat aag aag cac cac tac cgg gag ctg cct gca gag gtg          2850
Ala Met Arg Asn Lys Lys His His Tyr Arg Glu Leu Pro Ala Glu Val
            905                 910                 915 cgg gag acg ctg ggg acc ctc ccc gac gac ttc gtg tgc tac ttc acg          2898
Arg Glu Thr Leu Gly Thr Leu Pro Asp Asp Phe Val Cys Tyr Phe Thr
            920                 925                 930 tct cgc ttc ccc cac ctc ctc gca cac acc tac cgg gcc atg gag ctg          2946
Ser Arg Phe Pro His Leu Leu Ala His Thr Tyr Arg Ala Met Glu Leu
935                 940                 945                 950 tgc agc cac gag aga ctc ttc cag ccc tac tac ttc cac gag ccc cca          2994
Cys Ser His Glu Arg Leu Phe Gln Pro Tyr Tyr Phe His Glu Pro Pro
                955                 960                 965 gag ccc cag ccc cca gtg act cca gac gcc ctc tgagcgaggg cggcccctct        3047
Glu Pro Gln Pro Pro Val Thr Pro Asp Ala Leu
            970                 975 gttctggtgg cccagctgt gactgagggc ctggtcacca caattagagc ttgatgcctc        3107
ccggctttgc agggagacca ggcttcccaa accaagtgcc ttgagctgcc tgctctgcag        3167
cccacagagg acagtgctga cccccaggaag tgggagaagt ggcccctcgt gacctacagg       3227
gaactgggaa gatgctggcc ccaaaagcct tacggtcatg atgtctgcaa aggagggcct        3287
cagagacagc gcgagtagca cccccagcca tctactggat aaacttgctt cagacttttt       3347
aaattcctgc ttaatgtcag tctacaggcc tttcaggaag ggagaggagg gaatcgtaca       3407
ttttgcttgc gtgctgggac agctaggctg agatgcacca agtacagcct tcactggaga       3467
ccggaattga gaggtggggg atgctgagga gggggaggac ggagttcaga gggtgtcgtc       3527
```

```
ctgcagtatg agatttctca ttgatcacag atgtgcccag agtagcccag gtcactgtta   3587
actagtgttt ctgcagaggc agcaggagcc agcccggaat tc                      3629
```

<210> SEQ ID NO 2
<211> LENGTH: 977
<212> TYPE: PRT
<213> ORGANISM: Homo sapiens

<400> SEQUENCE: 2

Met Pro Ala Arg Arg Leu Leu Leu Leu Thr Leu Leu Leu Pro Gly
1               5                   10                  15

Leu Gly Ile Phe Gly Ser Thr Ser Thr Val Thr Leu Pro Glu Thr Leu
                20                  25                  30

Leu Phe Val Ser Thr Leu Asp Gly Ser Leu His Ala Val Ser Lys Arg
            35                  40                  45

Thr Gly Ser Ile Lys Trp Thr Leu Lys Glu Asp Pro Val Leu Gln Val
        50                  55                  60

Pro Thr His Val Glu Glu Pro Ala Phe Leu Pro Asp Pro Asn Asp Gly
65                  70                  75                  80

Ser Leu Tyr Thr Leu Gly Ser Lys Asn Asn Glu Gly Leu Thr Lys Leu
                85                  90                  95

Pro Phe Thr Ile Pro Glu Leu Val Gln Ala Ser Pro Cys Arg Ser Ser
                100                 105                 110

Asp Gly Ile Leu Tyr Met Gly Lys Lys Gln Asp Ile Trp Tyr Val Ile
            115                 120                 125

Asp Leu Leu Thr Gly Glu Lys Gln Gln Thr Leu Ser Ser Ala Phe Ala
130                 135                 140

Asp Ser Leu Cys Pro Ser Thr Ser Leu Leu Tyr Leu Gly Arg Thr Glu
145                 150                 155                 160

Tyr Thr Ile Thr Met Tyr Asp Thr Lys Thr Arg Glu Leu Arg Trp Asn
                165                 170                 175

Ala Thr Tyr Phe Asp Tyr Ala Ala Ser Leu Pro Glu Asp Glu Gly Asp
            180                 185                 190

Tyr Lys Met Ser His Phe Val Ser Asn Gly Asp Gly Leu Val Val Thr
        195                 200                 205

Val Asp Ser Glu Ser Gly Asp Val Leu Trp Ile Gln Asn Tyr Ala Ser
210                 215                 220

Pro Val Val Ala Phe Tyr Val Trp Gln Arg Glu Gly Leu Arg Lys Val
225                 230                 235                 240

Met His Ile Asn Val Ala Val Glu Thr Leu Arg Tyr Leu Thr Phe Met
                245                 250                 255

Ser Gly Glu Val Gly Arg Ile Thr Lys Trp Lys Tyr Pro Phe Pro Lys
            260                 265                 270

Glu Thr Glu Ala Lys Ser Lys Leu Thr Pro Thr Leu Tyr Val Gly Lys
        275                 280                 285

Tyr Ser Thr Ser Leu Tyr Ala Ser Pro Ser Met Val His Glu Gly Val
    290                 295                 300

Ala Val Val Pro Arg Gly Ser Thr Leu Pro Leu Leu Glu Gly Pro Gln
305                 310                 315                 320

Thr Asp Gly Val Thr Ile Gly Asp Lys Gly Glu Cys Val Ile Thr Pro
                325                 330                 335

Ser Thr Asp Val Lys Phe Asp Pro Gly Leu Lys Ser Lys Asn Lys Leu
            340                 345                 350

Asn Tyr Leu Arg Asn Tyr Trp Leu Leu Ile Gly His His Glu Thr Pro

-continued

```
            355                 360                 365
Leu Ser Ala Ser Thr Lys Met Leu Glu Arg Phe Pro Asn Asn Leu Pro
        370                 375                 380
Lys His Arg Glu Asn Val Ile Pro Ala Asp Ser Glu Lys Lys Ser Phe
385                 390                 395                 400
Glu Glu Val Ile Asn Leu Val Asp Gln Thr Ser Glu Asn Ala Pro Thr
                405                 410                 415
Thr Val Ser Arg Asp Val Glu Lys Pro Ala His Ala Pro Ala Arg
                420                 425                 430
Pro Glu Ala Pro Val Asp Ser Met Leu Lys Asp Met Ala Thr Ile Ile
                435                 440                 445
Leu Ser Thr Phe Leu Leu Ile Gly Trp Val Ala Phe Ile Ile Thr Tyr
        450                 455                 460
Pro Leu Ser Met His Gln Gln Gln Leu Gln His Gln Gln Phe Gln
465                 470                 475                 480
Lys Glu Leu Glu Lys Ile Gln Leu Leu Gln Gln Gln Gln Gln Gln Leu
                485                 490                 495
Pro Phe His Pro Pro Gly Asp Thr Ala Gln Asp Gly Glu Leu Leu Asp
                500                 505                 510
Thr Ser Gly Pro Tyr Ser Glu Ser Ser Gly Thr Ser Ser Pro Ser Thr
        515                 520                 525
Ser Pro Arg Ala Ser Asn His Ser Leu Cys Ser Gly Ser Ser Ala Ser
        530                 535                 540
Lys Ala Gly Ser Ser Pro Ser Leu Glu Gln Asp Asp Gly Asp Glu Glu
545                 550                 555                 560
Thr Ser Val Val Ile Val Gly Lys Ile Ser Phe Cys Pro Lys Asp Val
                565                 570                 575
Leu Gly His Gly Ala Glu Gly Thr Ile Val Tyr Arg Gly Met Phe Asp
                580                 585                 590
Asn Arg Asp Val Ala Val Lys Arg Ile Leu Pro Glu Cys Phe Ser Phe
        595                 600                 605
Ala Asp Arg Glu Val Gln Leu Leu Arg Glu Ser Asp Glu His Pro Asn
        610                 615                 620
Val Ile Arg Tyr Phe Cys Thr Glu Lys Asp Arg Gln Phe Gln Tyr Ile
625                 630                 635                 640
Ala Ile Glu Leu Cys Ala Ala Thr Leu Gln Glu Tyr Val Glu Gln Lys
                645                 650                 655
Asp Phe Ala His Leu Gly Leu Glu Pro Ile Thr Leu Leu Gln Gln Thr
                660                 665                 670
Thr Ser Gly Leu Ala His Leu His Ser Leu Asn Ile Val His Arg Asp
        675                 680                 685
Leu Lys Pro His Asn Ile Leu Ile Ser Met Pro Asn Ala His Gly Lys
        690                 695                 700
Ile Lys Ala Met Ile Ser Asp Phe Gly Leu Cys Lys Lys Leu Ala Val
705                 710                 715                 720
Gly Arg His Ser Phe Ser Arg Arg Ser Gly Val Pro Gly Thr Glu Gly
                725                 730                 735
Trp Ile Ala Pro Glu Met Leu Ser Glu Asp Cys Lys Glu Asn Pro Thr
                740                 745                 750
Tyr Thr Val Asp Ile Phe Ser Ala Gly Cys Val Phe Tyr Tyr Val Val
        755                 760                 765
Ser Glu Gly Ser His Pro Phe Gly Lys Ser Leu Gln Arg Gln Ala Asn
770                 775                 780
```

```
Ile Leu Leu Gly Ala Cys Ser Leu Asp Cys Leu His Pro Glu Lys His
785                 790                 795                 800

Glu Asp Val Ile Ala Arg Glu Leu Ile Glu Lys Met Ile Ala Met Asp
            805                 810                 815

Pro Gln Lys Arg Pro Ser Ala Asn Asp Val Leu Lys His Pro Phe Phe
            820                 825                 830

Trp Ser Leu Glu Lys Gln Leu Gln Phe Phe Gln Asp Val Ser Asp Arg
            835                 840                 845

Ile Glu Lys Glu Ser Leu Asp Gly Pro Ile Val Lys Gln Leu Glu Arg
850                 855                 860

Gly Gly Arg Ala Val Val Lys Met Asp Trp Arg Glu Asn Ile Thr Asp
865                 870                 875                 880

Pro Leu Gln Thr Asp Leu Arg Lys Phe Arg Thr Tyr Lys Gly Gly Ser
            885                 890                 895

Val Arg Asp Leu Leu Arg Ala Met Arg Asn Lys Lys His His Tyr Arg
            900                 905                 910

Glu Leu Pro Ala Glu Val Arg Glu Thr Leu Gly Thr Leu Pro Asp Asp
            915                 920                 925

Phe Val Cys Tyr Phe Thr Ser Arg Phe Pro His Leu Leu Ala His Thr
930                 935                 940

Tyr Arg Ala Met Glu Leu Cys Ser His Glu Arg Leu Phe Gln Pro Tyr
945                 950                 955                 960

Tyr Phe His Glu Pro Pro Glu Pro Gln Pro Val Thr Pro Asp Ala
            965                 970                 975

Leu

<210> SEQ ID NO 3
<211> LENGTH: 983
<212> TYPE: PRT
<213> ORGANISM: Caenorhabditis elegans

<400> SEQUENCE: 3

Met Arg Ala Thr Phe His Leu Phe Thr Phe Ile Phe Leu Leu Leu Phe
1               5                   10                  15

Ser Ser Val Ile Cys Ile Ser Thr Pro Gly Phe Arg Asn Asp His Glu
            20                  25                  30

Ser Ile Gly Asp Asp Glu Glu Lys Thr Ser Thr Ile Leu Val Ser
        35                  40                  45

Thr Ile Asp Gly Arg Leu Arg Ala Leu Asp Ser Glu Thr Gly Glu Ile
    50                  55                  60

Lys Trp Thr Leu Gln Glu Glu Pro Val Leu Arg Ser Pro Ser Ala Val
65                  70                  75                  80

Lys Gln Gly Phe Thr Phe Leu Pro Asn Pro Leu Asp Gly Ser Leu Tyr
            85                  90                  95

Val Leu Lys Asn Ser Ser Leu Lys Lys Leu Pro Phe Asn Ile Pro Gln
            100                 105                 110

Leu Val His Ala Ser Pro Cys Lys Gly Asn Asp Gly Ile Leu Tyr Ala
            115                 120                 125

Gly Ser Lys Lys Asp Val Trp Phe Gly Ile Asp Pro Lys Thr Gly Leu
130                 135                 140

Lys Val Glu Tyr Ile Leu Leu Asn Ile Ser Asp Lys Ile Leu Phe Leu
145                 150                 155                 160

Gln Val Glu Thr Leu Ser Ser Ala Ser Ala Asp Arg Ile Cys Pro Ala
            165                 170                 175
```

```
Asn Gln Lys Gln Thr Ile Phe Leu Gly Arg Thr Glu Tyr Arg Val Ser
            180                 185                 190

Met Phe Asp Glu Lys Asn Arg Gly Lys Thr Trp Asn Ala Thr Phe Asn
            195                 200                 205

Asp Tyr Ser Ala His Leu Leu Pro Glu Val Asn Thr Trp Pro Phe Lys
            210                 215                 220

His Tyr Ala Ser Ser His Gly Tyr Ile Leu Thr Phe Asp Arg Glu
225                 230                 235                 240

Thr Gly Glu Met Arg Trp Glu Gln Asp Leu Lys Gln Pro Val Val Ala
            245                 250                 255

Leu Tyr Leu Leu Arg Asp Asp Gly Leu His Lys Leu Pro Phe Glu Val
            260                 265                 270

Met Gly Lys Glu Thr Met Glu Asn Val Ala Lys Asn Ile Phe Thr Val
            275                 280                 285

Asp Gln Trp Pro Thr Val Leu Gly Val Asn Ala Ala Asp Pro Gln Thr
            290                 295                 300

Thr Ser Leu Thr Asn Gln Phe Phe Pro Ala Leu Phe Val Gly Glu Ser
305                 310                 315                 320

Ser Phe Gly Leu Tyr Ala Ile Glu Ala Leu Val Asp His Gln Thr Ile
            325                 330                 335

Thr Tyr Ser Pro Lys Leu Leu Gly Pro Leu Leu Glu Gly Pro Ala
            340                 345                 350

Pro Ile Ala Leu Thr Glu Met Glu Lys Glu Glu Tyr Leu Pro Pro Arg
            355                 360                 365

Arg Pro Ile Ile Arg Asn Ile Pro Pro Ser Ile Thr His Lys Thr Ser
            370                 375                 380

Asp Gly Glu Tyr Leu Leu Leu Gly Tyr His Asp Arg Pro Met Met Thr
385                 390                 395                 400

Met Ala Thr Ile Ile Pro Thr Arg Tyr Pro Val Pro Gly Pro His Lys
            405                 410                 415

Ala Ile Gly Ser Thr Ile Glu Arg Pro Pro Gln Leu Leu Gly Pro
            420                 425                 430

Val Glu Pro Gln Lys His Glu Asp Thr Ser Phe Ile Leu Leu Leu
            435                 440                 445

Asn Asn His Pro Ile Pro Phe Tyr Ala Thr Leu Val Thr Met Phe Ala
            450                 455                 460

Leu Leu Leu Thr Val Ile Trp Gln Cys Gly Arg Gln Trp Asp Gln Gln
465                 470                 475                 480

Lys Ser Thr Ser Arg Met Asp Ser Phe Glu Ile Val Asn Asn Pro Gly
            485                 490                 495

Glu Ser Arg Ser Ala Gln Thr Ser Lys Gln Ser Asn Arg Gly Ser Phe
            500                 505                 510

Gly Trp Ala Asn Arg Lys Ile Glu Ile Pro Glu Gly Trp Met Ala Val
            515                 520                 525

Gly Ser Lys Leu Met Tyr Ser Pro Ser Asp Ile Leu Gly Thr Gly Cys
            530                 535                 540

Glu Gly Thr Val Val Tyr Arg Gly Thr Phe Asp Gly Arg Glu Val Ala
545                 550                 555                 560

Val Lys Arg Val Val Ser Glu Phe Val Lys Phe Ala His Arg Glu Ala
            565                 570                 575

Asp Leu Leu Arg Glu Ser Asp Thr His Pro His Val Ile Arg Tyr Phe
            580                 585                 590
```

```
Cys Met Glu Ser Asp Ser Gln Phe Arg Tyr Leu Ala Leu Glu Leu Cys
        595                 600                 605

Ile Ala Ser Leu Asn Asp Tyr Val Glu Gln Lys Glu Val Gln Gln Asn
    610                 615                 620

Val Thr Ile Ala Leu Arg Asp Ile Met Lys Gln Ala Thr Asp Gly Leu
625                 630                 635                 640

Ala His Leu His Ala Ser Lys Ile Val His Arg Asp Met Lys Pro Gln
                645                 650                 655

Asn Val Leu Ile Thr Met Ala Ser Gln Arg Gly Glu Met Arg Ala Val
            660                 665                 670

Ile Ser Asp Phe Gly Leu Cys Lys Arg Val Gln Pro Gly Lys Asn Ser
        675                 680                 685

Ile Ser Arg Gly Ile Ala Ser Gly Leu Ala Gly Thr Asp Gly Trp Ile
    690                 695                 700

Ala Pro Glu Val Leu Ile Ser Ala Ser Thr Ser Tyr Pro Val Asp Ile
705                 710                 715                 720

Phe Ser Leu Gly Cys Ile Phe Tyr Tyr Val Leu Thr Ser Gly Thr His
                725                 730                 735

Pro Phe Gly Lys Ser Leu His Arg Gln Ala Asn Ile Val Asn Gly Glu
            740                 745                 750

Tyr Thr Leu Asn Lys Leu Ala Asp Leu Asp Asp Trp Ser Leu Ala Asp
        755                 760                 765

Asp Leu Ile Ser Ser Met Leu Asn Val Glu Pro Leu His Arg Leu Thr
    770                 775                 780

Ala Asp Ala Val Leu Asn His Pro Phe Phe Trp Thr Ser Glu Lys Arg
785                 790                 795                 800

Leu Ala Tyr Phe Ser Asp Val Ser Asp Arg Val Glu Lys Glu Glu Asp
                805                 810                 815

Asn Ser Pro Val Val Arg Arg Ile Glu Thr Asp Ala Arg Ile Val Val
            820                 825                 830

Cys Gly Gly Trp Arg Glu Lys Ile Cys Asp Ala Leu Lys Glu Asp Leu
        835                 840                 845

Arg Lys Phe Arg Thr Tyr Lys Ser Phe Ser Val Arg Asp Leu Leu Arg
    850                 855                 860

Ala Met Arg Asn Lys Lys His His Tyr Arg Glu Leu Pro Glu Asp Val
865                 870                 875                 880

Arg Gln Ser Leu Gly Asp Ile Pro Asp Gln Phe Leu His Tyr Phe Thr
                885                 890                 895

Ser Arg Phe Pro Arg Leu Leu Leu His Val Tyr Lys Ala Thr Glu Tyr
            900                 905                 910

Cys Ser Gly Glu Ala Val Phe Lys Arg Tyr Tyr Ser Asp Asp Val Arg
        915                 920                 925

Ala Arg Met Tyr Pro Ile Val Glu Glu Glu Arg Val Arg Lys Lys
    930                 935                 940

Ile Lys Glu Glu Met Ala Asn Glu Val Trp Ala Arg Ala Pro Lys Pro
945                 950                 955                 960

Val Glu Gln Arg Thr Pro Leu Lys Leu Asp Lys Arg Asn Ile Lys Lys
                965                 970                 975

Lys Ser Asn Pro Asn Thr Asp
            980

<210> SEQ ID NO 4
<211> LENGTH: 443
<212> TYPE: PRT
```

<213> ORGANISM: Saccharomyces cerevisiae

<400> SEQUENCE: 4

```
Leu Val Val Ser Cys Lys Ile Leu Gly Tyr Gly Ser Ser Gly Thr Val
 1               5                  10                  15

Val Phe Gln Gly Ser Phe Gln Gly Arg Pro Val Ala Val Lys Arg Met
            20                  25                  30

Leu Ile Asp Phe Cys Asp Ile Ala Leu Met Glu Ile Lys Leu Leu Thr
        35                  40                  45

Glu Ser Asp Asp His Pro Asn Val Ile Arg Tyr Tyr Cys Ser Glu Thr
    50                  55                  60

Thr Asp Arg Phe Leu Tyr Ile Ala Leu Glu Leu Cys Asn Leu Asn Leu
65                  70                  75                  80

Gln Asp Leu Val Glu Ser Lys Asn Val Ser Asp Glu Asn Leu Lys Leu
                85                  90                  95

Gln Lys Glu Tyr Asn Pro Ile Ser Leu Leu Arg Gln Ile Ala Ser Gly
           100                 105                 110

Val Ala His Leu His Ser Leu Lys Ile Ile His Arg Asp Leu Lys Pro
       115                 120                 125

Gln Asn Ile Leu Val Ser Thr Ser Arg Phe Thr Ala Asp Gln Gln
   130                 135                 140

Thr Gly Ala Glu Asn Leu Arg Ile Leu Ile Ser Asp Phe Gly Leu Cys
145                 150                 155                 160

Lys Lys Leu Asp Ser Gly Gln Ser Ser Phe Arg Thr Asn Leu Asn Asn
                165                 170                 175

Pro Ser Gly Thr Ser Gly Trp Arg Ala Pro Glu Leu Leu Glu Glu Ser
            180                 185                 190

Asn Asn Leu Gln Cys Gln Val Glu Thr Glu His Ser Ser Arg His
        195                 200                 205

Thr Val Val Ser Ser Asp Ser Phe Tyr Asp Pro Phe Thr Lys Arg Arg
    210                 215                 220

Leu Thr Arg Ser Ile Asp Ile Phe Ser Met Gly Cys Val Phe Tyr Tyr
225                 230                 235                 240

Ile Leu Ser Lys Gly Lys His Pro Phe Gly Asp Lys Tyr Ser Arg Glu
                245                 250                 255

Ser Asn Ile Ile Arg Gly Ile Phe Ser Leu Asp Glu Met Lys Cys Leu
            260                 265                 270

His Asp Arg Ser Leu Ile Ala Glu Ala Thr Asp Leu Ile Ser Gln Met
        275                 280                 285

Ile Asp His Asp Pro Leu Lys Arg Pro Thr Ala Met Lys Val Leu Arg
    290                 295                 300

His Pro Leu Phe Trp Pro Lys Ser Lys Lys Leu Glu Phe Leu Leu Lys
305                 310                 315                 320

Val Ser Asp Arg Leu Glu Ile Glu Asn Arg Asp Pro Pro Ser Ala Leu
                325                 330                 335

Leu Met Lys Phe Asp Ala Gly Ser Asp Phe Val Ile Pro Ser Gly Asp
            340                 345                 350

Trp Thr Val Lys Phe Asp Lys Thr Phe Met Asp Asn Leu Glu Arg Tyr
        355                 360                 365

Arg Lys Tyr His Ser Ser Lys Leu Met Asp Leu Leu Arg Ala Leu Arg
    370                 375                 380

Asn Lys Tyr His His Phe Met Asp Leu Pro Glu Asp Ile Ala Glu Leu
385                 390                 395                 400
```

-continued

```
Met Gly Pro Val Pro Asp Gly Phe Tyr Asp Tyr Phe Thr Lys Arg Phe
            405                 410                 415

Pro Asn Leu Leu Ile Gly Val Tyr Met Ile Val Lys Glu Asn Leu Ser
        420                 425                 430

Asp Asp Gln Ile Leu Arg Glu Phe Leu Tyr Ser
        435                 440

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Primer

<400> SEQUENCE: 5

Ile Ser Asp Phe Gly Leu Cys Lys
 1               5

<210> SEQ ID NO 6
<211> LENGTH: 9
<212> TYPE: DNA
<213> ORGANISM: Artificial Sequence
<220> FEATURE:
<223> OTHER INFORMATION: Description of Artificial Sequence: Primer

<400> SEQUENCE: 6 cgccatgcc                                                                 9

<210> SEQ ID NO 7
<211> LENGTH: 24
<212> TYPE: DNA
<213> ORGANISM: Artificial Sequence
<220> FEATURE:
<221> NAME/KEY: misc_feature
<222> LOCATION: 1
<223> OTHER INFORMATION: N may be Thymine or Cytosine
<220> FEATURE:
<221> NAME/KEY: misc_feature
<222> LOCATION: 4,9,13,16
<223> OTHER INFORMATION: N may be Adenine or Guanine
<220> FEATURE:
<221> NAME/KEY: misc_feature
<222> LOCATION: 7,10,19,22
<223> OTHER INFORMATION: N may be any nucleotide
<220> FEATURE:
<221> NAME/KEY: misc_feature
<222> LOCATION: 21
<223> OTHER INFORMATION: N may be Adenine or Thymine
<220> FEATURE:
<223> OTHER INFORMATION: Description of Artificial Sequence: Primer

<400> SEQUENCE: 7
nttnctntnn ccnaantcng nnat                                               24

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Primer

<400> SEQUENCE: 8

Ile Ser Asp Phe Gly Leu Cys Lys
 1               5

<210> SEQ ID NO 9
<211> LENGTH: 28
<212> TYPE: DNA
```

```
<213> ORGANISM: Artificial Sequence
<220> FEATURE:
<223> OTHER INFORMATION: Description of Artificial Sequence: Primer

<400> SEQUENCE: 9
gctctagaac catgccggcc cggcggct                                              28

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 10
aggctgccat cattaggatc t                                                     21

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 11
cattgatgtg catcaccttc ctc                                                   23

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 12
cggaattcat cacctatccc ctgagcatg                                             29

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 13
cggaattctc agagggcgtc tggagtca                                              28
```

DNA ENCODING THE NOVEL MAMMALIAN PROTEIN, IRE1P

RELATED APPLICATIONS

This application is a continuation of U.S. Ser. No. 09/357,273, filed on Jul. 20, 1999, now abandoned and claims priority from U.S. Ser. No. 60/093,526, filed on Jul. 21, 1998, the contents of which are incorporated herein by reference.

FIELD OF THE INVENTION

The present invention relates generally to novel polynucleotides and the proteins encoded thereby and more particularly, to polynucleotides encoding a novel mammalian bifunctional protein kinase/endoribonuclease (Ire1p), and therapeutic, diagnostic and research methods employing same.

BACKGROUND OF THE INVENTION

The endoplasmic reticulum (ER) is an organelle specialized for protein folding and assembly of membrane proteins and of proteins destined for trafficking tolysosomes and the extracellular space. Newly synthesized lysosomal, secretory, and membrane proteins are translocated into the lumen of the ER that provides an oxidizing environment and contains a multitude of ER resident proteins that facilitate the folding process (reviewed by Gething and Sambrook, *Nature* 355:34-44 (1992); Hartl, F. U., *Nature* 381:571-579 (1996)). The transcription of many of the genes encoding ER resident proteins, such as BiP (immunoglobulin binding protein or GRP78), is upregulated in response to glucose deprivation (Lee, A. S., *Trends Biochem. Sci.* 12:20-30 (1987)), in response to conditions that disrupt protein folding in the ER, and in response to the presence of unfolded or unassembled proteins in the ER. Lee, A. S., *Trends Biochem. Sci.* 12:20-30 (1987); Kozutsumi, Y. et al., *Nature* 332:462-464 (1988); Dorner, A. J. et al., *J. Biol. Chem.* 264:20602-20607 (1989). Thus, an unfolded protein response (UPR) exists in cells that detects unfolded protein in the ER lumen to transduce a signal(s) across the ER membrane to activate transcription of selective genes in the nucleus. Kozutsumi, Y. et al., *Nature* 332:462-464 (1988).

Although little is known about the mechanism of the UPR signal transduction pathway in higher eukaryotes, studies from the budding yeast, *Saccharomyces cerevisiae*, demonstrate the existence of a complex unique signaling pathway between these two organelles. Mori, K. et al., *EMBO J.* 11:2583-2593 (1992). Characterization of the promoters of the genes encoding ER resident proteins e.g. KAR2 (yeast BiP), demonstrated that they share a highly conserved cis-acting regulatory Unfolded Protein Responsive Element (UPRE), that is necessary and sufficient to mediate the response to unfolded protein in the ER. Mori, K. et al., *Cell* 74:743-756 (1993); Cox, J. S. et al., *Cell* 73:1197-1206 (1993). By using genetic approaches, Ire1p/Ern1p, an ER type 1 transmembrane protein that contains a Ser/Thr protein kinase domain in its carboxy terminus, was identified as the UPR proximal sensor that monitors the status of unfolded protein inside the ER lumen. Cox, J. S. et al., *Cell* 73:1197-1206 (1993); Mori, K. et al., *Cell* 74:743-756 (1993). Ire1p was originally identified as a gene required for inositol prototrophy in *S. cerevisiae*. Nikawa, J. et al., *Mol. Microbiol.* 6:1441-1446 (1992). The kinase activity of Ire1p is essential to transmit the UPR signal from the ER to induce specific gene transcription in the nucleus. Mori, K. et al., *Cell* 74:743-756 (1993); Shamu, C. E. et al., *EMBO J.* 15:3028-3039 (1996). Cox and Walter (*J. Biol. Chem.* 264:20602-20607 (1996)) subsequently reported that Ire1p directly regulated biosynthesis of Hac1p, a transcription factor that binds specifically to the UPRE. Recent studies demonstrate that HAC1 mRNA is synthesized as a precursor that is inefficiently translated. Upon activation of the UPR, Ire1p elicits an endonuclease activity that specifically cleaves an intron from HAC1 mRNA. Subsequently, the tRNA ligase Rlg1p is required to splice together the 5' and 3' cleaved fragments to yield a product that is efficiently translated. Cox, J. S. et al., *J Biol. Chem.* 264:20602-20607 (1996); Sidrauski, K. et al., *Cell* 90:1031-1039 (1997); Kawahara, T. et al., *Mol. Biol. Cell* 8:1845-1862 (1997); Chapman, R. E. et al., *Curr. Biol.* 7:850-859 (1997)). The increased level of Hac1p leads to the transcriptional activation of genes containing a UPRE.

While the molecular mechanisms signaling the yeast UPR are well characterized, the mechanisms signaling the UPR in mammalian cells remain elusive. A conserved promoter region, the glucose-regulated core sequence, in several mammalian genes encoding for ER proteins was identified as a potential cis-acting regulatory element equivalent to the yeast.UPRE. Resendez, E. J. et al., *Mol. Cell. Biol.* 8:4579-4584 (1988). Despite the sequence similarity between the mammalian glucose-regulated core sequence and the *S. cerevisiae* UPRE, no single element in this promoter region appears necessary and sufficient to mediate transcriptional induction as described for the UPRE in yeast cells. In addition, although transcriptional activation in response to conditions that disrupt protein folding in the ER correlates with changes in activities of protein kinases and phosphatases (Resendez. E. et al., *J. Cell Biol.* 103:2145-2152 (1986); Koong et al. 1994; Cao, X. et al., *J. Biol. Chem.* 270:494-502 (1995); Chen, K. et al., *J. Biol. Chem.* 273:749-755 (1998)), a signaling molecule that responds to unfolded protein in the ER to induce transcription of the ER protein chaperone genes has not been identified.

It would thus be desirable to provide a mammalian signaling molecule that responds to unfolded protein in the ER to induce transcription of the ER protein chaperone genes. It would also be desirable to identify and characterize the human gene product that is equivalent to Ire1p of *S. cerevisiae* and functions as a proximal sensor for the UPR in mammalian cells. It would further be desirable to provide a method for protecting cells from the stressful condition of unfolded protein in the ER.

SUMMARY OF THE INVENTION

A novel polynucleotide encoding a mammalian bifunctional protein kinase\endoribonuclease referred to herein as hIre1p, is provided. hIre1p is expressed in the endoplasmic reticulum (ER) and upregulates the transcription of genes encoding ER protein chaperones, such as, but not limited to, glucose-related proteins (GRP's).

hIre1p is a type 1 transmembrane protein containing a cytoplasmic domain that is highly conserved to the yeast counterpart having a Ser/Thr protein kinase domain and a domain homologous to RNase L. However, the luminal domain has extensively diverged from the yeast gene product. hIre1p expressed in mammalian cells displays intrinsic autophosphorylation activity and an endoribonuclease activity that cleaves the 5' splice site of yeast HAC1 mRNA, a substrate for the endoribonuclease activity of yeast Ire1p.

Over-expressed hIre1p is localized to the ER with particular concentration around the nuclear envelope and some co-localization with the nuclear pore complex. Expression of hIRE1 mRNA is autoregulated through a process that requires a functional hIre1p kinase activity. Over-expression of wild-type hIre1p constitutively activates a reporter gene under transcriptional control of the rat BiP promoter, whereas expression of a catalytically inactive hIre1p acts in a trans-dominant negative manner to prevent transcriptional activation of the BiP promoter in response to ER stress induced by inhibition of N-linked glycosylation.

Signaling mechanism(s) by which cells respond to ER stress have important therapeutic implications. Expression of Ire1p results in induction of GRPs, including BiP and GRP94, protecting cells from death induced by calcium release from the ER (Morris, J. A. et al., *J. Biol. Chem.* 272:4327-4334 (1997)), oxidative stress (Gomer, C. J. et al., *Cancer Res.* 51:6574-6579 (1991)), and anti-cancer treatments such as adriamycin and topoisomerase inhibitors. Shen, J. et al., *Proc. Natl. Acad. Sci. USA* 84:3278-3282 (1987); Hughes, C. S. et al., *Cancer Res.* 49:4452-4454 (1989). Conversely, inhibiting expression of Ire1p inhibits induction of GRP and increases sensitivity of a cell to death in response to calcium release from the ER (Li, X. A. et al., *Mol. Cell. Biol.* 11:3446-3453 (1991); Li, X. A. et al., *J. Cell Physiol.* 153:575-582 (1992)), oxidative stress (Gomer, C. J. et al., *Cancer Res.* 51:6574-6579 (1991)), hypoxia (Koong et al. 1994), and T cell mediated cytotoxicity. Sugawara, S. et al., *Cancer Res.* 53:6061-6005 (1993). Thus, methods for protecting cells from death by increasing expression of hIRE1, as well as methods for increasing sensitivity of a cell to death by inhibiting expression of hIRE1, are provided.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings.

(A) Alignment and restriction map of overlapping complementary DNAs encoding human Ire1p. RH3 was the primary probe used to screen a human fetal liver cDNA library to obtain cDNA clones 3-1-1, 3-1.2, 8-1, 9-1, 13-1 and 17-1. F14 was a 5' RACE-PCR product amplified from RNA isolated from the human hepatoma cell line HepG2. An open box represents the predicted open reading frame coding for hIre1p.

(B) Domain organization of hIre1p. Solid box, a potential signal sequence; ⊠1, potential N-linked glycosylation site; TM, a putative transmembrane region; Linker, a region having not homology to known proteins; S/T kinase, catalytic domain of Ser/Thr protein kinase; RNase L, a domain having high homology to 2-5 oligo-A-dependent RNase. The % identity to the corresponding domains of *S. cerevisiae* and *C. elegans* is indicated.

(C) Amino acid sequence alignment of human Ire1p (H.s.), *S. cerevisiae* Ire1p (S.c.) and its putative homologous protein from *C. elegans* (C.e.). (SEQ ID Nos:2, 4 and 3, respectively). Open boxes indicate the identical sequence. Shaded boxes indicate conserved residues. Dashes represent gaps between residues in order to obtain maximum matching. Numbers are the position of the last amino acid. ∇, potential signal peptide cleavage site; •, invariant residues in protein kinase domain; ★, indicates the invariant Lys599 residue in kinase subdomain II. The glutamine rich cluster (I) and the serine rich cluster (II) in the linker region are also identified.

Figure 2:
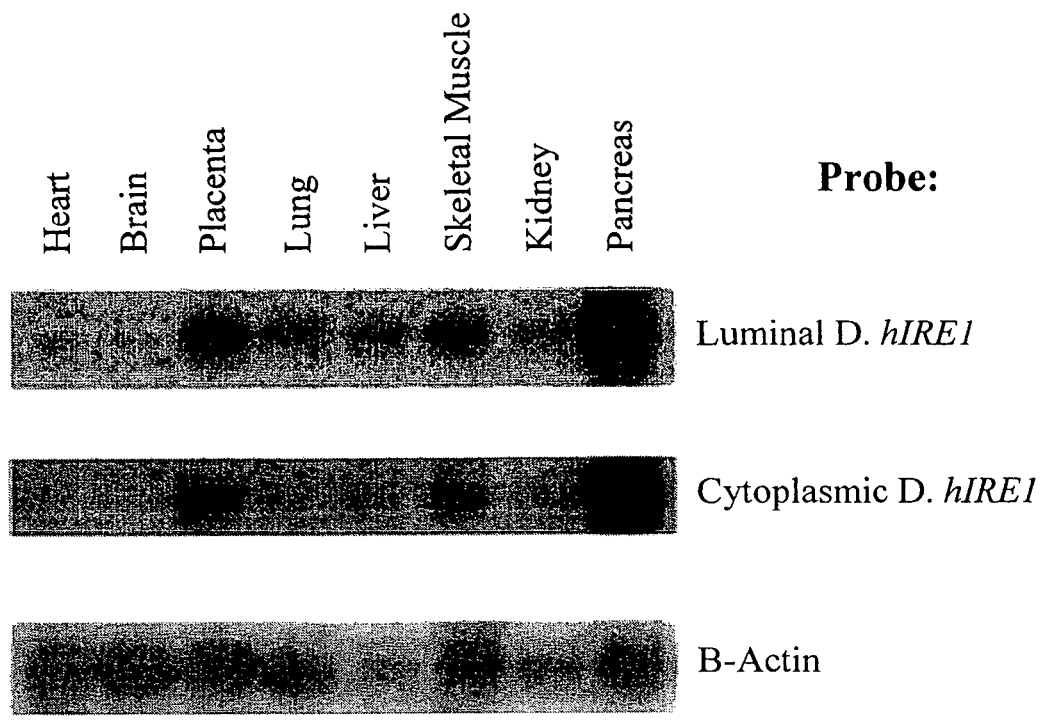

FIG. 2. hIRE1 is ubiquitously expressed in human tissues. Northern blot analysis of poly (A)$^+$ RNA isolated from various human tissues (Clontech) by hybridization with $^{32}$P-labeled-cDNA probes corresponding to the hIRE1 luminal domain, the hIRE1 cytoplasmic domain, or human β-actin cDNA. Exposure of the Ire1 autoradiogram was 24-fold longer than that of β-actin.

FIG. 3. Over-expression of hIre1p in transiently transfected COS-1 monkey cells.

(A) hIre1p expression in transfected COS-1 cells. COS-1 cells were transiently transfected with or without expression plasmids encoding wild-type hIre1p (pED-hIRE1) or its kinase defective mutant (pED-hIRE1 K599A). Transfected cells were pulse-labeled with [$^{35}$S]-methionine and cysteine for 15 min. Cell extracts were prepared and equal amounts were immunoprecipitated with α-hIre1p antibodies and analyzed by SDS-PAGE and autoradiography.

(B) Expression of eIF-2α in co-transfected cells. COS-1 cells were mock-transfected (lane 1) or co-transfected with pED-eIF-2α in the presence of pED (lane 2), pED-hIRE1 (lane 3) or pED-hIRE1 K599A (lane 4). The cells were pulse-labeled with [$^{35}$S]-methionine and cysteine for 15 min. Cell extracts were prepared and equal cpm of radiolabeled protein were analyzed directly by SDS-PAGE and autoradiography.

(C) Functional hIre1p limits accumulation of hIRE1 mRNA. Total RNA was isolated from COS-1 cells transfected with pED, pED-hIRE1 or pED-hIRE1 K599A plasmid and treated in the presence (+) or absence (−) of cycloheximide. RNA samples (10 µg) were resolved in a formaldehyde agarose gel, blotted onto nylon membrane and hybridized with $^{32}$P-labeled hIRE1 cDNA probe. Arrow indicates the hIRE1 transcript.

(D) hIre1p has intrinsic kinase activity. Wild-type or K599A mutant hIre1p were immunoprecipitated from transiently transfected COS-1 cells. Mock represents cells that did not receive plasmid DNA. The proteins were incubated in kinase buffer in the presence of [γ-$^{32}$P]-ATP at 30° C. for 40 min. The proteins were resolved by SDS-PAGE and transferred to a nitrocellulose membrane. The upper panel represents incorporation of $^{32}$P phosphate into hIre1p determined by autoradiography. The lower panel represents the Ire1p protein level determined by western blot analysis using α-hIre1p antibodies and alkaline phosphatase staining. The amount of K599A mutant hIre1p loaded onto the gel is ⅓ the amount of the immunoprecipitated proteins loaded for lanes 1 and 2. Therefore, the amount of steady state K599A mutant hIre1p is approximately 10-fold greater than the wild-type hIre1p.

FIG. 4. hIre1p is a site-specific endoribonuclease.

(A) In vitro cleavage of yeast HAC1 mRNA by hIre1p. An in vitro transcribed [$^{32}$P]-labeled HAC1 mRNA was incubated with *E. coli*-expressed GST or GST-Ire1p adsorbed to glutathione beads or with COS-1 cell-expressed hIre1p or hIre1p K599A protein adsorbed to protein A-sepharose beads. After the indicated period of time, the cleavage products were analyzed by electrophoresis on a 5% denaturing polyacrylamide gel. Schemes on the left depict the predicted cleavage products. Numbers on the right indicate predicted base pair size of RNA products expected based on yeast HAC1 mRNA cleavage by yeast Ire1p. (Sidrauski, K. et al., *Cell* 90:1031-1039 (1997).

(B) hIre1p cleaves yeast HAC1 mRNA at residue G661. The HAC1 RNA cleavage site was mapped using in vitro transcribed HAC1 mRNA after incubation with GST, GST-Ire1p, hIre1p or hIre1p K599A as described in panel A. The products were reverse transcribed with Superscript II Reverse Transcriptase (Bethesda Research Labs) using oligonucleotide primer complementary to the intron of HAC1 RNA. Sequencing ladders on the left represent HAC1 DNA sequence determined with the same primer. Arrow indicates the position of primer extended products.

Figure 5:
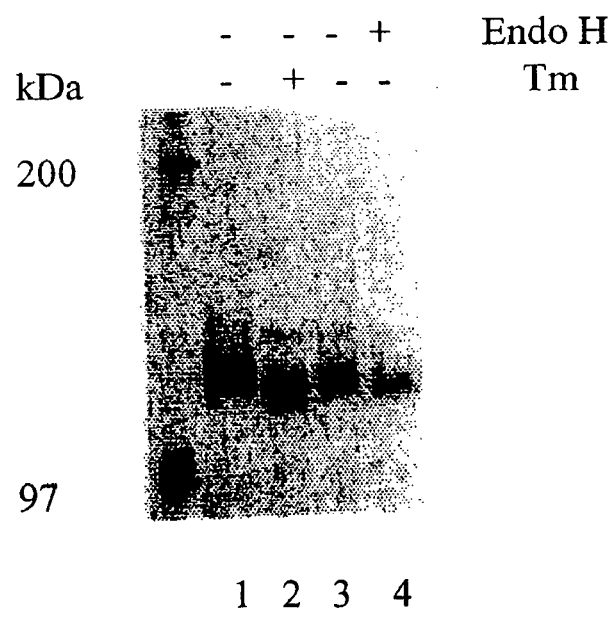

FIG. 5. hIre1p contains high-mannose core oligosaccharides.

Transfected COS-1 cells that over-express hIre1p were pulse-labeled with [$^{65}$S]-methionine and cysteine for 15 min in the presence (lane 2) or absence (lane 1) of tunicamycin and cell extracts were prepared. In parallel, cells pulse-labeled 15 min in the absence of tunicamycin were incubated 3 hr in medium containing excess unlabeled methionine and cysteine before harvesting cell extracts. The [$^{65}$S]-labeled hIre1p was immunoprecipitated from cell extracts and analyzed by SDS-PAGE. Prior to SDS-PAGE, immunoprecipitated samples were incubated in the absence (lanes 1-3) or presence (lane 4) of endoglycosidase H.

Figure 6C:
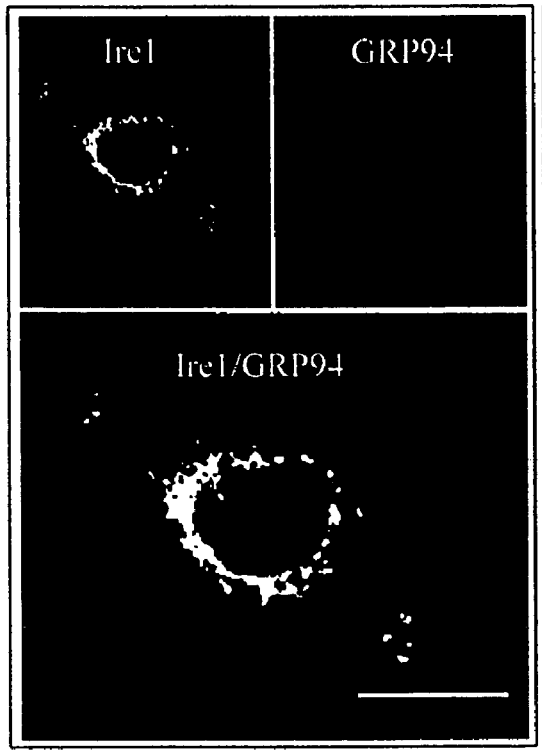
Figure 6C:
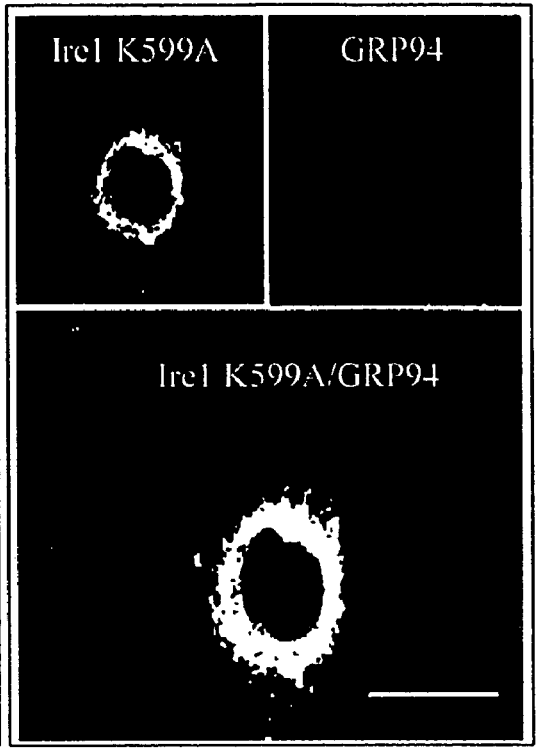
Figure 6C:
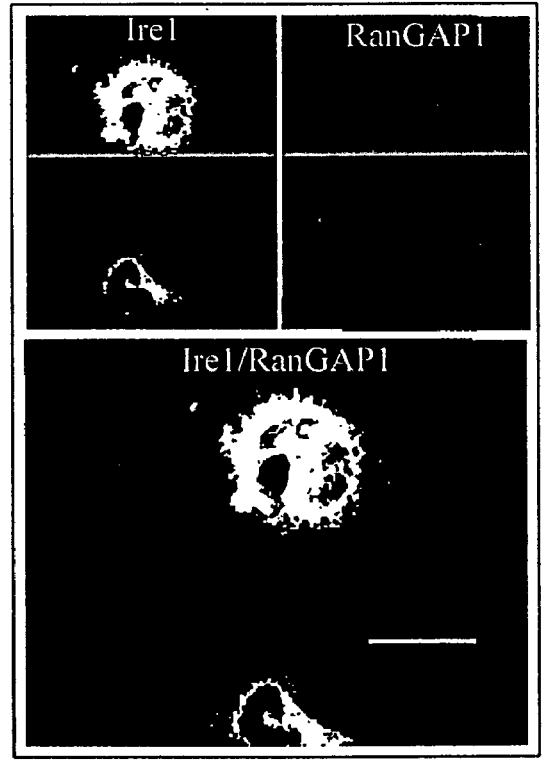

FIG. 6. Confocal laser scanning fluorescence microscopy of hIre1p expressed in COS-1 cells.

The subcellular localization of hIre1p in transfected COS-1 cells was determined by immunofluorescence using mouse α-hIre1p. COS-1 cells transfected with wild-type (A) or K599A mutant (B) IRE1 expression plasmids were double labeled with mouse α-hIre1p and rabbit α-GRP94. Transfected COS-1 cells transfected with wild-type IRE1 expression plasmid were double labeled with mouse α-hIre1 p and guinea pig α-RanGAP1 (C). Secondary antibodies used were either rhodamine-conjugated goat α-rabbit or rhodamine-conjugated goat α-guinea pig (red) in the presence of fluorescein-conjugated goat α-mouse (green). The images were merged where colocalization is shown in yellow. Cells were viewed and digitally photographed with a Bio-Rad confocal fluorescence microscope. The bar represents 25 μm.

Figure 7:
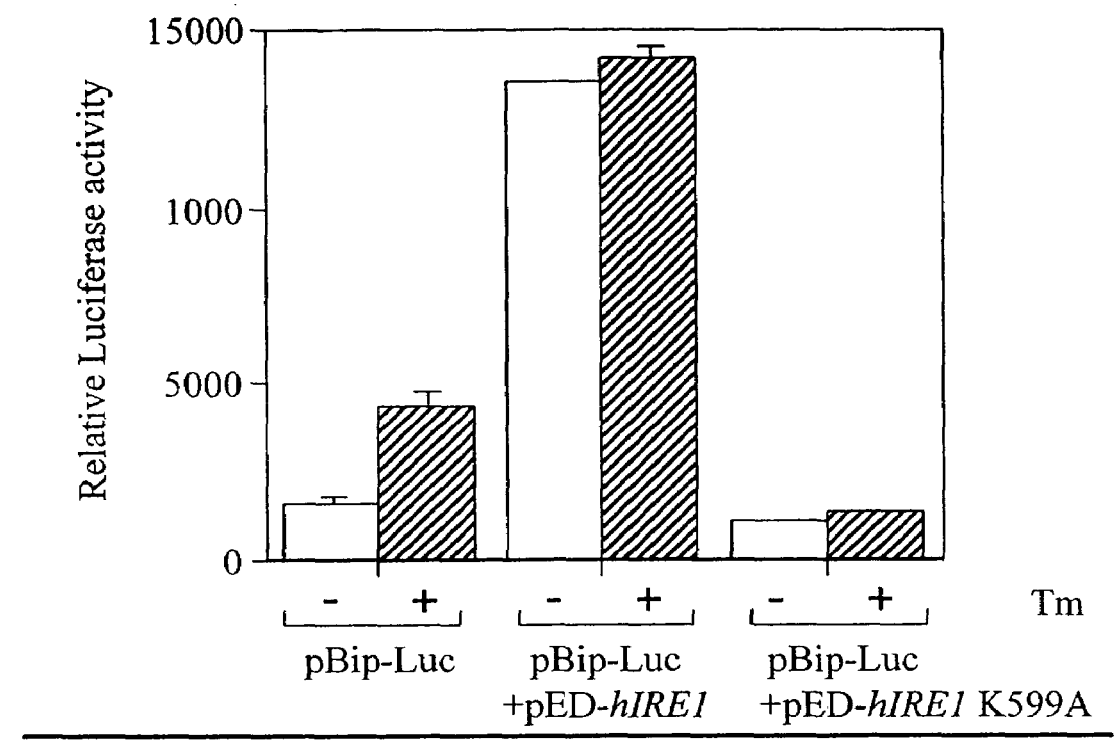

FIG. 7. hIre1p-dependent induction of UPR in mammalian cells.

The activation of the unfolded protein response was measured by co-transfection of COS-1 cells with a luciferase reporter plasmid under control of the rat BiP promoter, RSV-β-gal and either pED-hIRE1 or pED-hIRE1 K599A plasmid DNAs. At 60 hr post-transfection, the cells were treated with 10 μg/ml tunicamycin for 6 hr. The luciferase activity was determined from triplicate independent transfection experiments and was normalized to β-galactosidase activity to correct for transfection efficiency.

FIGS. 8A-8B. The nucleotide sequence of hIRE1 of the present invention (SEQ ID NO:1). The sequence information has been submitted to GenBank under accession no. AF059198 and is expressly incorporated by reference.

FIG. 9. The amino acid sequence of hIre1p of the present invention (SEQ ID NO:2). See also, Tirasophon, W. et al., Genes Dev. 12:1812-1824 (1998), expressly incorporated by reference.

DETAILED DESCRIPTION OF THE PREFERRED EMBODIMENTS

A novel mammalian bifunctional protein kinase/endoribonuclease referred to herein as hIre1p, is provided. Also provided is a novel cDNA (hIRE1) encoding hIre1p. The isolated cDNA is about 3.6 kbp long with an open reading frame extending from nucleotide 97 to 3030, encoding the novel mammalian protein, hIre1p.

The nucleic acid sequence of the cDNA encoding Ire1p and its deduced amino acid sequence are set forth in FIGS. 8A-8B and FIG. 9, respectively. In a preferred embodiment, the isolated nucleic acid molecule of the invention comprises the nucleotide sequence of FIGS. 8A and 8B, or homologues therefore. In another preferred embodiment, the isolated and purified polypeptide of the invention comprises the amino acid sequence of FIG. 9, as well as biological equivalents.

Mammalian hIre1p is constitutively expressed in all tissues and is believed to be a functional homologue of the yeast Ire1p, for the following reasons. First, hIre1p and yeast Ire1p are both type 1 transmembrane proteins in which the carboxy terminal domains are 34% identical at the amino acid level. Although the amino terminal halves of these two proteins have extensively diverged, the amino terminal half of hIre1p is 37% identical to a *C. elegans* putative gene product having a similar domain organization as hIre1p. The cytoplasmic domain of hIre1p contains all the conserved subdomains present in Ser/Thr protein kinases and a carboxy terminal tail that displays greater homology to human RNase L than *S. cerevisiae* Ire1p. Second, hIre1p displays both intrinsic kinase activity measured by autophosphorylation capability and an endoribonuclease activity that specifically cleaved the 5' splice site of *S. cerevisiae* HAC1 mRNA at the same nucleotide, guanine 661, as the *S. cerevisiae* Ire1p. Third, over-expressed hIre1p is specifically localized to the ER, with particular concentration around the nuclear envelope. Fourth, over-expression of wild-type hIre1p constitutively activates a marker gene under control of the rat BiP promoter. Finally, over-expression of a catalytically inactive kinase mutant K599A completely prevents induction by tunicamycin, a treatment that promotes accumulation of unfolded protein in the ER.

Without intending to be bound by theory, it is believed that hIre1p functions as the proximal sensor for the mammalian unfolded protein response (UPR). hIre1p induces the expression of protein chaperones of the endoplasmic reticulum, and in particular, expression of glucose-related proteins (GRPs), including, without limitation, BiP and GRP94. Thus, by increasing the expression of hIRE1 in a cell or providing increased quantities of hIre1p, expression of protein chaperones in said cell may be upregulated. Upregulation of protein chaperone expression can protect cells from death induced by calcium release from the ER, oxidative stress and anti-cancer treatments such as adriamycin and topoisomerase inhibitors. Conversely, by inhibiting the expression of hIRE1, expression of the protein chaperones may also be down regulated. Inhibition of GRP induction increases sensitivity of cells to death in response to calcium release from the ER, oxidative stress, hypoxia and T cell mediated cytotoxicity.

Fragments of the protein of the present invention which are capable of exhibiting biological activity are also encompassed by the present invention. Fragments of the protein may be in linear form or they may be cyclized using known methods, for example, as described in H. U. Saragovi, et al., *BioTechnology* 10:773-778 (1992) and in R. S. McDowell et al., *J. Amer. Chem. Soc.* 114:9245-9253 (1992). Such fragments may be fused to carrier molecules such as immunoglobulins for many purposes, including increasing the valency of protein binding sites. For example, fragments of the protein may be fused through "linker" sequences to the Fc portion of an immunoglobulin. For a bivalent form of the protein, such a fusion could be to the Fc portion of an IgG molecule. Other immunoglobulin isotypes may also be used to generate such fusions. For example, a protein-IgM fusion would generate a decavalent form of the protein of the invention.

The present invention also provides a gene corresponding to the cDNA sequence disclosed herein. The corresponding gene can be isolated in accordance with known methods using the sequence information disclosed herein. Such methods include the preparation of probes or primers from the disclosed sequence information for identification and/or amplification of genes in appropriate genomic libraries or other sources of genomic materials.

In another aspect, DNA sequence information provided by the present invention allows for the preparation of relatively short DNA (or RNA) sequences or probes that are identical to or hybridize to the nucleotide sequence disclosed herein. Nucleic acid probes (also referred to as oligonucleotide probes) of an appropriate length are prepared based on a consideration of the nucleotide sequence of FIGS. 8A and 8B. The probes can be used in a variety of assays appreciated by those skilled in the art, for detecting the presence of complementary sequences in a given sample. The probes may be useful in research, prognostic and diagnostic applications. For example, the probes may be used to detect homologus nucleotide sequences, e.g., the human homolog. The design of the probe should preferably follow these parameters:

a) it should be designed to an area of the sequence which has the fewest ambiguous bases ("N's"), if any; and b) it should be designed to have a $T_m$ of approximately 80° C. (assuming 2 degrees for each A or T and 4 degrees for each G or C). The oligonucleotide should preferably be labeled with $\gamma$-$^{32}$P ATP (specific activity 6000 Ci/mole) and T4 polynucleotide kinase using commonly employed techniques for labeling oligonucleotides. Other labeling techniques can also be used. Unincorporated label should preferably be removed by gel filtration chromatography or other established methods. The amount of radioactivity incorporated into the probe should be quantitated by measurement in a scintillation counter. Preferably, specific activity of the resulting probe should be approximately 4e+6 dpm/mole.

A further preferred nucleic acid sequence employed for hybridization studies or assays includes probe molecules that are complementary to at least a 10 to 70 or so long nucleotide stretch of the polynucleotide sequence shown in FIGS. 8A and 8B. A size of at least 10 nucleotides in length helps to ensure that the fragment will be of sufficient length to form a duplex molecule that is both stable and selective. Molecules having complementary sequences over stretches greater than 10 bases in length are generally preferred in order to increase stability and selectivity of the hybrid, and thereby improve the quality and degree of specific hybrid molecules obtained. It will be appreciated that nucleic acid molecules having gene-complementary stretches of 25 to 40 nucleotides, 55 to 70 nucleotides, or even longer where desired, may be preferred. Such fragments can be readily prepared by, for example, directly synthesizing the fragment by chemical means, by application of nucleic acid reproduction technology, such as the PCR technology of U.S. Pat. No. 4,683,202, or by excising selected DNA fragments from recombinant plasmids containing appropriate inserts and suitable restriction enzyme sites. In certain embodiments, it is also advantageous to use oligonucleotide primers. The sequence of such primers is designed using the polynucleotide of the present invention and is used with PCR technology.

The invention also encompasses allelic variants of the disclosed polynucleotide or protein; that is, naturally-occurring alternative forms of the isolated polynucleotide which also encode proteins which are identical, homologous or related to that encoded by the polynucleotide.

The isolated polynucleotide of the invention may be operably linked to an expression control sequence such as the pMT2 or pED expression vectors disclosed in Kaufman et al., Nucleic Acids Res. 19:4485-4490 (1991), in order to produce the protein recombinantly. Many suitable expression control sequences are known in the art. General methods of expressing recombinant proteins are also known and are exemplified in R. Kaufman, Methods in Enzymology 185:537-566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae*, *Schizosaccharomyces pombe*, *Kluyveromyces* strains, *Candida*, or any yeast strain capable of expressing heterologous proteins. Potentially suitable bacterial strains include *Escherichia coil*, *Bacillus subtills*, *Salmonella typhimurium*, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit) and such methods are well known in the art, as described in Summers and Smith, *Texas Agricultural Experiment Station Bulletin No. 1555* (1987). As used herein, an insect cell capable of expressing a polynucleotide of the present invention is "transformed."

The protein of the invention may be prepared by culturing transformed host cells under culture conditions suitable to express the recombinant protein. The resulting expressed protein may be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST), hexahistidine or thioredoxin (TRX). Kits for expression and purification of such fusion proteins are commercially available from New England BioLab (Beverly, Mass.), Pharmacia (Piscataway, N.J.) and InVitrogen, respectively. The protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The protein of the invention may also be expressed as a product of transgenic animals, e.g., as a component of the milk of transgenic cows, goats, pigs, or sheep which are characterized by somatic or germ cells containing a nucleotide sequence encoding the protein.

The protein may also be produced by known conventional chemical synthesis. Methods for constructing the protein of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified protein in screening of therapeutic compounds and in immunological processes for the development of antibodies.

The protein provided herein also include protein characterized by amino acid sequences similar to those of purified protein but into which modifications are naturally provided or deliberately engineered. For example, modifications in the peptide of DNA sequences can be made by those skilled in the art using known techniques. Modifications of interest in the protein sequence may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein.

Other fragments and derivatives of the sequence of the protein which would be expected to retain protein activity in whole or in part may thus be useful for screening or other immunological methodologies may also be easily made by those skilled in the art given the disclosures herein. Such modifications are believed to be encompassed by the present invention.

In one embodiment, the present invention provides an antibody immunoreactive with the hIre1p polypeptide. Also contemplated by the present invention are antibodies immunoreactive with homologues or biologically equivalent polynucleotides and polypeptides of the present invention. As used herein, the term "antibody" is used in its broadest sense to include polyclonal and monoclonal antibodies, as well as polypeptide fragments of antibodies that retain a specific binding activity for hIre1p. One skilled in the art will appreciate that anti-hIre1p antibody fragments such as Fab, F(ab)$_2$ and Fv fragments can retain specific binding activity for hIre1p and, thus, are included within the definition of an antibody. In addition, the term "antibody" as used herein includes naturally occurring antibodies as well as non-naturally occurring antibodies and fragments that retain binding activity. Methods of making antibodies are known in the art. See, e.g., Harlow and Lane, *Antibodies: A Laboratory Manual* (Cold Spring Harbor Press, 1988).

As used herein, the term "nucleic acid" is intended to mean natural and synthetic linear and sequential arrays of nucleotides and nucleosides, e.g. in cDNA, genomic DNA (gDNA), mRNA, and RNA, oligonucleotides, oligonucleosides and derivatives thereof. It will also be appreciated that such nucleic acids can be incorporated into other nucleic acid chains referred to as "vectors" by recombinant-DNA techniques such as cleavage and ligation procedures. The terms "fragment" and "segment" are as used herein with reference to nucleic acids (e.g., cDNA, genomic DNA, i.e., gDNA) are used interchangeably to mean a portion of the subject nucleic acid such as constructed artificially (e.g. through chemical synthesis) or by cleaving a natural product into a multiplicity of pieces (e.g. with a nuclease or endonuclease to obtain restriction fragments). As used herein, "A" represents adenine; "T" represents thymine; "G" represents guanine; "C" represents cytosine; and "U" represents uracil.

As referred to herein, the term "encoding" is intended to mean that the subject nucleic acid may be transcribed and translated into the subject protein in a cell, e.g. when the subject nucleic acid is linked to appropriate control sequences such as promoter and enhancer elements in a suitable vector (e.g. an expression vector) and the vector is introduced into a cell. The term "polypeptide" is used to mean three or more amino acids linked in a serial array.

As referred to herein, the term "capable of hybridizing under high stringency conditions" means annealing a strand of DNA complementary to the DNA of interest under highly stringent conditions. Likewise, "capable of hybridizing under low stringency conditions" refers to annealing a strand of DNA complementary to the DNA of interest under low stringency conditions. In the present invention, hybridizing under either high or low stringency conditions would involve hybridizing a nucleic acid sequence (e.g., the complementary sequence to FIGS. 8A and 8B or portion thereof), with a second target nucleic acid sequence. "High stringency conditions" for the annealing process may involve, for example, high temperature and/or low salt content, which disfavor hydrogen bonding contacts among mismatched base pairs. "Low stringency conditions" would involve lower temperature, and/or lower salt concentration than that of high stringency conditions. Such conditions allow for two DNA strands to anneal if substantial, though not near complete complementarity exists between the two strands, as is the case among DNA strands that code for the same protein but differ in sequence due to the degeneracy of the genetic code. Appropriate stringency conditions which promote DNA hybridization, for example, 6×SSC at about 45° C., followed by a wash of 2×SSC at 50° C. are known to those skilled in the art or can be found in *Current Protocols in Molecular Biology*, John Wiley & Sons, NY (1989), 6.31-6.3.6. For example, the salt concentration in the wash step can be selected from a low stringency of about 2×SSC at 50° C. to a high stringency of about 0.2×SSC at 50° C. In addition, the temperature in the wash step can be increased from low stringency at room temperature, about 22° C., to high stringency conditions, at about 75° C. Other stringency parameters are described in Maniatis, T., et al., *Molecular Cloning: A Laboratory Manual*, Cold Spring Harbor Laboratory Press Cold Spring N.Y., (1982), at pp. 387-389; see also Sambrook J. et al., *Molecular Cloning: A Laboratory Manual*, Second Edition, Volume 2, Cold Spring Harbor Laboratory Press, Cold Spring, N.Y. at pp. 8.46-8.47 (1989).

As used herein, the term "specifically binds" refers to a non-random binding reaction between two molecules, for example between an antibody molecule immunoreacting with an antigen.

The term "knockout" refers to partial or complete suppression of the expression of at least a portion of a protein encoded by an endogenous DNA sequence in a cell. The term "knockout construct" refers to a nucleic acid sequence that is designed to decrease or suppress expression of a protein encoded by endogenous DNA sequences in a cell. The nucleic acid sequence used as the knockout construct is typically comprised of 1) DNA from some portion of the gene (exon sequence, intron sequence, and/or promoter sequence) to be suppressed and 2) a marker sequence used to detect the presence of the knockout construct in the cell. Typically, the knockout construct is inserted into an embryonic stem cell (ES cell) and is integrated into the ES cell genomic DNA, usually by the process of homologous recombination. This ES cell is then injected into, and integrates with, the developing embryo.

The phrases "disruption of the gene" and "gene disruption" refer to insertion of a nucleic acid sequence into one region of the native DNA sequence (usually one or more exons) and/or the promoter region of a gene so as to decrease or prevent expression of that gene in the cell as compared to the wild-type or naturally occurring sequence of the gene. By way of example, a nucleic acid construct can be prepared containing a DNA sequence encoding an antibiotic resistance gene which is inserted into the DNA sequence that is complementary to the DNA sequence (promoter and/or coding region) to be disrupted. When this nucleic acid construct is then transfected into a cell, the construct will integrate into the genomic DNA. Thus, many progeny of the cell will no longer express the gene at least in some cells, or will express it at a decreased level, as the DNA is now disrupted by the antibiotic resistance gene.

The term "marker sequence" refers to a nucleic acid sequence that is 1) used as part of a nucleic acid construct (i.e., the "knockout construct") to disrupt the expression of the gene(s) of interest (e.g., hIRE1), and 2) used as a means to identify those cells that have incorporated the knockout construct into the genome. The marker sequence may be any sequence that serves these purposes, although typically it will be a sequence encoding a protein that confers a detectable trait on the cell, such as an antibiotic resistance gene or an assayable enzyme not typically found in the cell. Where the marker sequence encodes a protein, the marker sequence will also typically contain a promoter that regulates its expression.

The term "progeny" refers to any and all future generations derived and descending from a particular mammal, i.e., a mammal containing a knockout construct inserted into its genomic DNA. Thus, progeny of any successive generation are included herein such that the progeny, the F1, F2, F3, generations and so on indefinitely are included in this definition.

The foregoing and other aspects of the invention may be better understood in connection with the following example, which is presented for purposes of illustration and not by way of limitation.

SPECIFIC EXAMPLE

I. Results

Figure 1A:
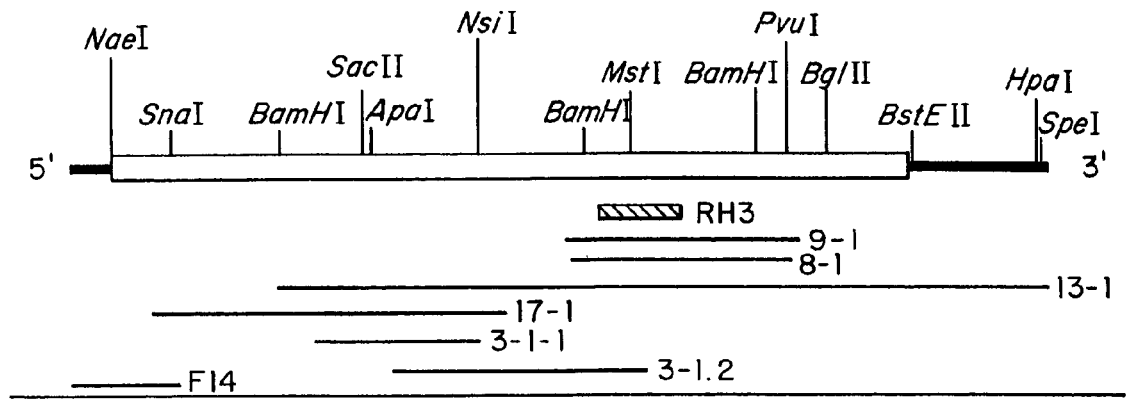
FIG. 1. Structure and amino acid sequence analysis of hIre1p.

Isolation of complementary DNA encoding human Ire1p. To screen for a human homologue of *S. cerevisiae* IRE1, degenerate oligonucleotide primers were designed from the amino acid sequence (ISDFGLCK) in the kinase subdomain VII of *S. cerevisiae* IRE1 that was also conserved in a putative *C. elegans* IRE1 identified in the genbank, but was not present in other protein Ser/Thr protein kinases. The oligonucleotide was used in combination with a λgt 10 specific primer to amplify DNA fragments from a human fetal liver cDNA library. RH3 was isolated as a candidate clone containing a 270 bp PCR product, that encoded for a portion of the catalytic domain of a novel human Ser/Thr protein kinase. The clone was used as a probe to screen for overlapping clones from a human fetal liver cDNA library (FIG. 1A). A 3.5 kb cDNA was assembled from overlapping clones that has a single open reading frame encoding 977 amino acid residues with a predicted molecular mass of 110 kDa (FIG. 1C). One clone had a 106 bp putative 5' untranslated region that did not contain either an ATG codon or an in frame termination codon upstream of the ATG codon having a favorable sequence context (CGCCATGCC) to serve as an initiation codon. Kozak, M., *Nucl. Acids Res.* 15:8125-8248 (1987). In addition, immediately following the putative initiation codon was a sequence of residues that are predicted to serve as a signal peptide, having positively charged residues at the extreme N-terminus followed by a core of hydrophobic residues and then turn inducing residues (Pro and Gly). Nielsen, H. et al., *Protein Eng.* 10:1-6 (1997). We predict that signal cleavage occurs after Gly18. Finally, one clone (13-1) was identified that contained a 3' untranslated region of 598 bp that contained multiple translation termination codons in all reading frames, but did not contain a conserved polyadenylation signal, suggesting additional sequence exists within the 3' untranslated region of the mRNA. On the basis of these observations, it is believed the intact coding region for this putative kinase is cloned.

A hydropathy plot of the deduced amino acid sequence revealed that it contained two stretches of hydrophobic residues: a leucine rich motif close to the amino terminus that could function as a signal sequence and a stretch of 21 consecutive hydrophobic residues lying approximately in the middle of the molecule that could provide a transmembrane domain. This suggested that the putative protein is a type 1 transmembrane protein with the kinase domain in the carboxy terminus and with a single potential N-linked glycosylation site (Asn-Ala-Thr) in the luminal domain at residue 176 (FIG. 1B).

Figure 1B:
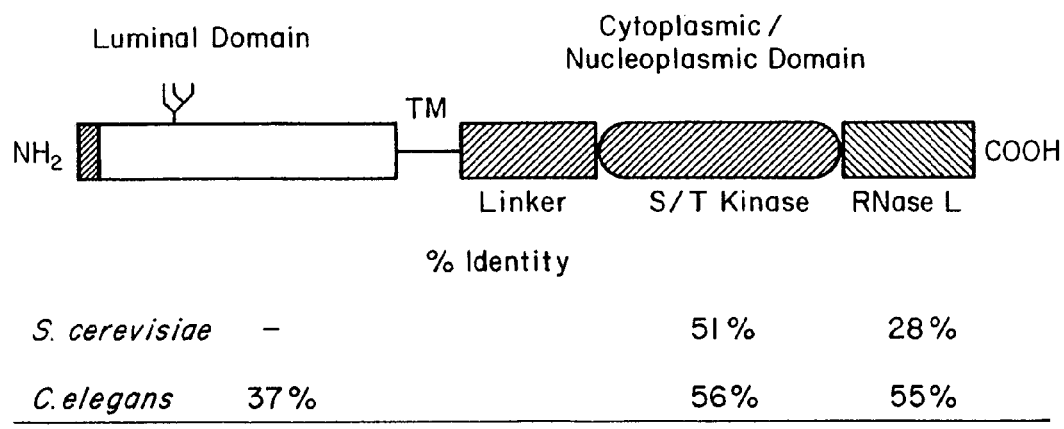

Searches of the protein sequence database suggested that the carboxy terminal half of the protein could be divided into 3 domains: a linker region, the putative Ser/Thr protein kinase domain, and an RNase L-like domain homologous to 2'-5' oligo A-dependent ribonuclease (FIG. 1B). The linker region is unique to the human protein and contains two subdomains rich in glutamine and serine residues, respectively. In contrast, the kinase domain displays high homology with both that of *S. cerevisiae* Ire1p and its putative counterpart from *C. elegans*, having conserved all 12 invariant residues that are present within the protein kinase superfamily (FIG. 1C). Hanks, S. K. et al., *FASEB J.* 9:576-596 (1995). The similarity among these three proteins also extends to the very carboxy terminal RNase L domain (FIG. 1C). Zhou A. et al., *Cell* 72:753-765 (1993). The cytoplasmic domain of hIre1p, as well as its putative counterpart from *C. elegans* do differ from yeast Ire1p in that they do not contain a potential nuclear localization signal and also lack an insertion of 30 hydrophilic amino acids between conserved kinase subdomains VIII and IX. Mori, K. et al., *Cell* 74:743-756 (1993). In contrast, the amino terminal half of the protein was less conserved, with the *C. elegans* protein and displayed no significant similarity with *S. cerevisiae* Ire1p. Based on the homologies within the cytoplasmic domain, this putative human protein is referred to as human Ire1p (hIre1p).

hIRE1 is constitutively expressed in all tissues The expression of endogenous hIRE1 was studied by Northern blot hybridization to $^{32}$P-labeled cDNA probes corresponding to either the luminal domain or the cytoplasmic domain of hIre1p. The hybridization patterns with these 2 probes were identical (FIG. 2). hIRE1 was ubiquitously expressed at low levels as detected by a single species of mRNA migrating at approximately 8 kb in all tissues examined. Based on the size of endogenous hIRE1 mRNA together with its predicted translation product, it is suggested that hIRE1 mRNA contains a long, approximately 4 kb, 3' untranslated region. Interestingly, the hIRE1 mRNA was most abundant in pancreatic tissue, suggesting that hIre1p might play a significant role in this particular organ.

hIre1p displays kinase activity that is required to down-regulate its synthesis. To examine the biochemical properties of hIre1p, antibodies were raised in mice immunized with a glutathione-S-transferase (GST)-hIre1p fusion protein. Although this polyclonal antibody reacted with the antigen against which it was raised, the antibody did not detect endogenous Ire1 p upon immunoprecipitation from several human cell lines, suggesting that the level of endogenous hIre1p is extremely low (data not shown). In order to obtain sufficient amount of protein for characterization, hIre1p was over-expressed in COS-1 monkey cells by transient DNA transfection of the cDNA cloned in the expression vector pED. Kaufman. R. J. et al., *Nucl. Acids Res.* 19:4485-4490 (1991). In addition, an expression vector encoding a kinase defective hIRE1 mutant was constructed in which the conserved lysine at residue 599 in the putative ATP binding site was substituted by alanine (pED-hIRE1 K599A). Hanks, S. K. et al., *Methods Enzymol.* 200:38-62 (1991). The expression of these proteins was monitored by immunoprecipitation of cell extracts from [$^{65}$S]-methionine and cysteine pulse-labeled cells using α-hIre1p antibody. As expected, both wild-type and K599A mutant hIre1p were expressed as 110 kDa proteins (FIG. 3A). This protein product was not detected from mock-transfected cells or from pED vector-transfected cells (FIG. 3A and data not shown). Interestingly, the level of mutant K599A hIre1p synthesis in transfected COS-1 cells was approximately 16 times higher than that of the wild-type hIre1p. The difference between wild-type and mutant hIre1p expression was not attributable to differences in transfection efficiency (determined by immunofluorescence) and different independent isolates of both plasmid DNAs yielded similar results. The increased synthesis of mutant hIre1p could account for the increased steady state level (approximately 10-fold from FIG. 3D), suggesting there is no significant difference in the rate of degradation.

The difference in the expression level between wild-type and the K599A mutant Ire1p protein in transfected COS-1 cells (FIG. 3A) lead to a speculation that hIre1p might auto-regulate its expression. Alternatively, over-expression of wild-type hIre1p may inhibit general expression in the subpopulation of transiently transfected cells due to general toxicity. To address this possibility, COS-1 cells were co-transfected with another marker gene encoding the eukaryotic translation initiation factor eIF-2α subunit (pED-eIF-2α) with either pED-hIRE1 or pED-hIRE1 K599A. The transfected cells were metabolically pulse-labeled with [$^{35}$S]-methionine and cysteine and protein synthesis was analyzed by SDS-PAGE of total cell extract samples. The presence of either hIre1p or its mutant (K599A) had no effect on the synthesis of eIF-2α, suggesting that wild-type hIre1p over-expression is not toxic and does not inhibit global gene expression in the transfected cells (FIG. 3B; compare lane 3 to lanes 2 and 4).

Figure 3C:
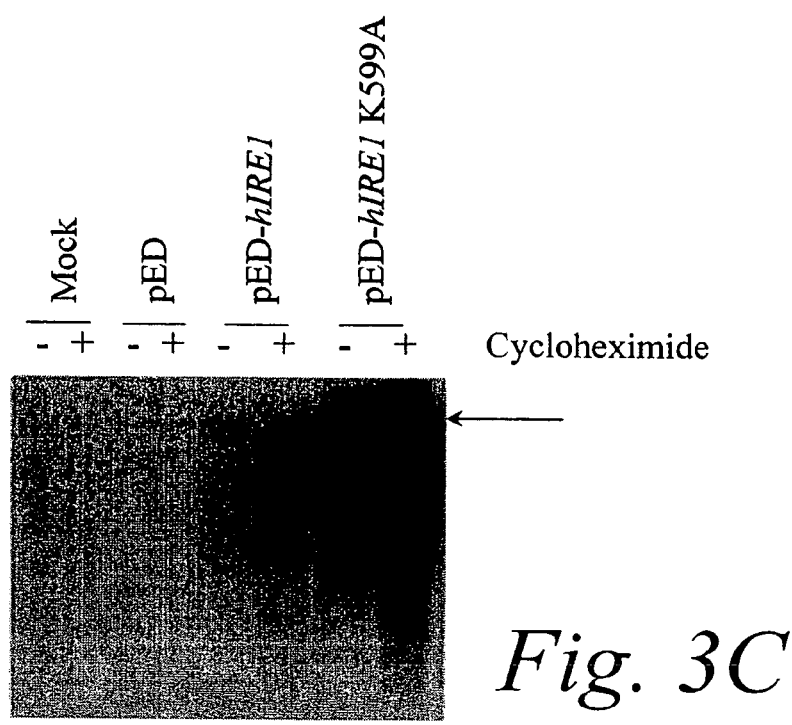

To further investigate the mechanism for the reduced expression of wild-type hIre1p, the level of plasmid derived hIRE1 mRNA from COS-1 transfected cells was analyzed. Total RNA was prepared from COS-1 cells transfected with pED, pED-hIRE1 or pED-hIRE1 K599A and treated in the presence or absence of cyclohexamide for 12 hr before harvesting RNA. Northern blot hybridization demonstrated the level of hIRE1 K599A mRNA was 10 times higher than the wild-type hIRE1 mRNA derived from the transfected DNA (FIG. 3C). Inhibition of protein synthesis by cyclohexamide had no effect on the steady state level of these mRNAs, suggesting that ongoing protein synthesis is not required to down-regulate hIRE1 mRNA. Taken together, it was concluded that functional hIre1p downregulates its own expression at the level of mRNA production and/or stability.

Figure 3D:
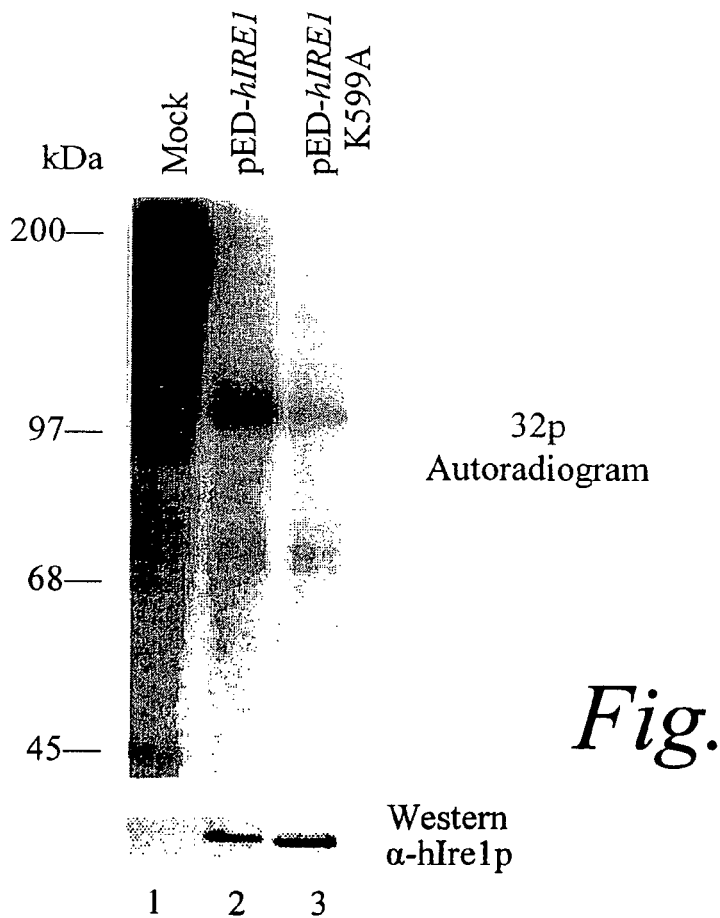
Figure 4A:
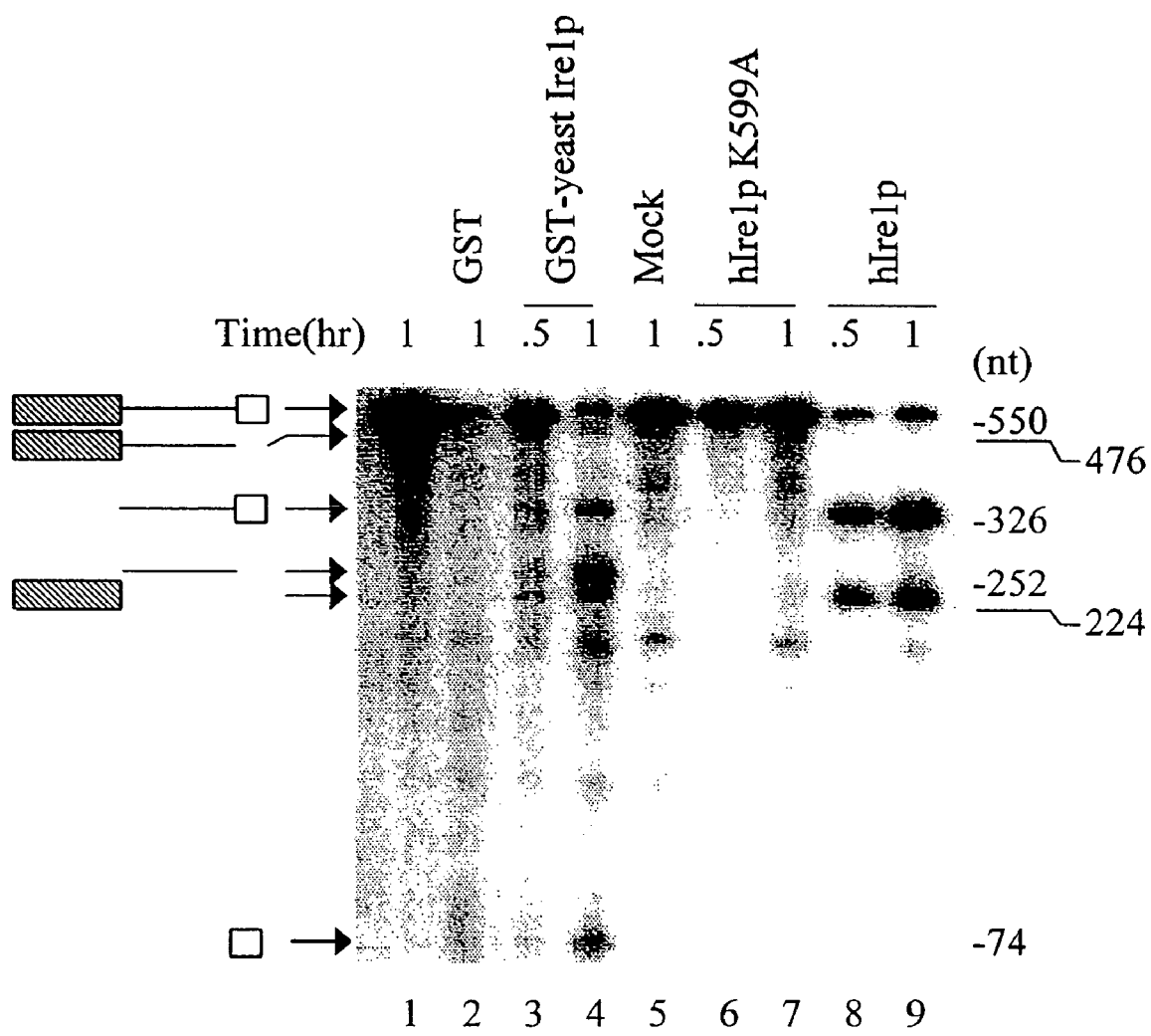

The deduced amino acid sequence of hIre1p suggested the presence of an intact catalytic Ser/Thr protein kinase domain. To demonstrate functional activity of the kinase, the capability for autophosphorylation was measured, since this activity correlates with functional activity of yeast Ire1p. Welihinda, A. A. et al., *J. Biol. Chem.* 271:18181-18187 (1996). The wild-type and mutant K599A hIre1p were immunoprecipitated from transfected COS-1 cells and incubated in kinase buffer with [γ-$^{32}$P]-ATP. The proteins were then resolved by SDS-PAGE and transferred onto a nitrocellulose membrane prior to autoradiography and probing with α-hIre1p antibody. The wild-type hIre1p was efficiently autophosphorylated (FIG. 3D). The phosphorylation resulted in a slightly slower mobility as determined by western blotting. Substitution of the conserved lysine residue in the putative ATP binding pocket with alanine significantly reduced the phosphorylation detected, especially when corrected for the greater amount of protein immunoprecipitated (FIG. 3D; compare lanes 2 and 3). The low level of phosphorylation of this mutant Ire1p may result from either the presence of endogenous COS-1 cell-derived Ire1p or another kinase(s) in the immunoprecipitation reaction. Taken together, it was concluded that hIre1p displays an intrinsic protein kinase activity.

hIre1p is a bifunctional enzyme having an endoribonuclease activity specific to yeast HAC1 mRNA. Sidrauski and Walter (*Cell* 90:1031-1039 (1997)) recently demonstrated that the cytoplasmic domain of yeast Ire1p exhibits a site-specific endoribonuclease activity capable of cleaving HAC1 mRNA at both the 5' and 3' splice site junctions in vitro. The proposed catalytic domain of RNase L indeed displays greater sequence similarity to hIre1p than to the yeast Ire1p. This led to the hypothesis that hIre1p might exhibit a similar endoribonuclease activity and may be able to catalyze the same specific RNA cleavage as observed for yeast Ire1p. Since the identity of the mammalian HAC1 homologue is unknown, it was determined whether yeast HAC1 mRNA could serve as a substrate to test for an endoribonuclease activity of hIre1p. A 550 nucleotide substrate derived from *S. cerevisiae* HAC1 mRNA that contained both the 5' and 3' splice site junctions was synthesized in vitro. Incubation of this substrate in the presence of a GST-yeast Ire1p fusion protein simultaneously cleaved the HAC1 mRNA substrate at the 5' and 3' splice site junctions, as previously shown by Sidrauski and Walter (1997). The cleavage generated 3 species of RNA products (corresponding to a 224 nt 5' exon, a 252 nt intron and a 74 nt 3' exon) and 2 intermediates (corresponding to a 476 nt 5'exon/intron and a 326 nt intron/3'exon) (FIG. 4A; lanes 3,4). The cleavage was not observed in the absence of GST-Ire1p, or with control GST protein alone (FIG. 4A; lanes 1,2). Surprisingly, hIre1p isolated by immunoprecipitation from transfected COS-1 cells that over-express hIre1p was able to catalyze cleavage, however, only two species of RNA products were observed in this reaction (FIG. 4A; lanes 8,9). The two products appeared to be the same size as those derived from GST-yeast Ire1p mediated cleavage at only the 5' splice site junction (representing the 224 nt 5' exon and the 326 nt intron/3' exon). Prolonged incubation of the substrate with hIre1p did not generate the intron or the 3' exon fragments (data not shown). In contrast, no cleavage was observed when the mutant K599A hIre1p was substituted for hIre1p (FIG. 4A; lanes 6,7). Taken together, it was concluded that hIre1p exhibits endoribonuclease activity and its intrinsic kinase activity is required to elicit the endoribonuclease activity.

Figure 4B:
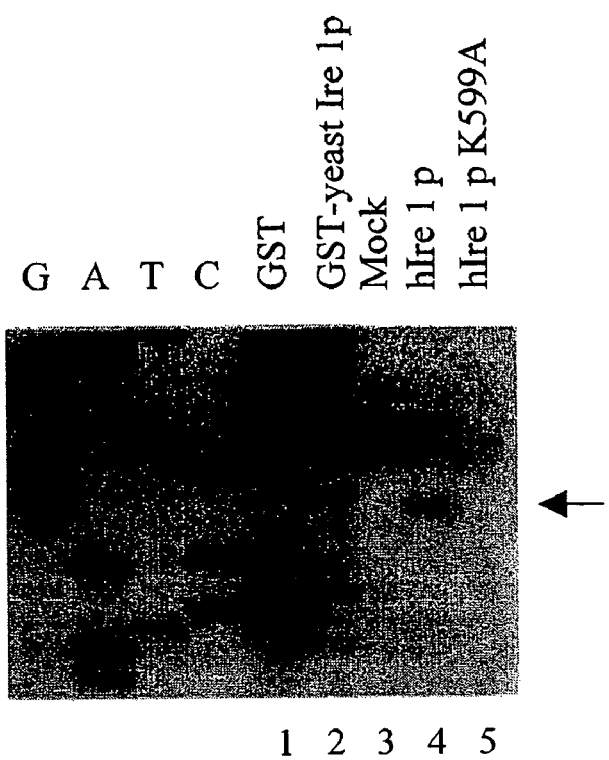

To precisely map the hIre1p cleavage site in HAC1 mRNA, primer extension analysis was performed. An antisense oligonucleotide complementary to the HAC1 intron was used to reverse transcribe HAC1 mRNA cleaved by either *E. coli* expressed GST-yeast Ire1p or hIre1p expressed and immunoprecipitated from transfected COS-1 cells. The same primer was also used to determine the nucleotide sequence of the HAC1 gene (FIG. 4B). The length of primer extended products derived from HAC1 mRNA cleaved with GST-yIre1p and hIre1p were identical, indicating that both GST-yeast Ire1p and hIre1p cleave HAC1 mRNA at the same position at the predicted 5'exon/intron junction (FIG. 4B; compare lanes 2 and 4). Comparison of these two extended products to the HAC1 DNA sequence ladder indicated that they both were terminated after the guanine at residue 661. In contrast, this primer extended product was not observed in the reverse transcription reactions of HAC1 mRNA incubated with control GST from *E. coli* or with control immunoprecipitated protein from either pED-hIRE1 K599A- or mock-transfected cells.

hIre1p is an ER membrane protein preferentially localized to the nuclear envelope. ER resident glycoproteins that do not transit to the Golgi complex have high mannose-containing oligosaccharides that are sensitive to digestion by endoglycosidase H. The presence of a single potential N-linked glycosylation site in the N-terminal domain of hIre1p was used to determine the subcellular localization of hIre1p. hIre1p immunoprecipitated from extracts prepared from metabolically labeled transfected cells treated with tunicamycin, a drug that inhibits addition of N-linked core oligosaccharides, displayed a slightly reduced molecular mass compared to Ire1p isolated from untreated cells, suggesting the absence of the single N-linked core oligosaccharide (FIG. 5; compare lanes 1 and 2). Treatment of immunoprecipitated hIre1p with endoglycosidase H decreased the molecular mass of the labeled hIre1p to that comparable to unglycosylated hIre1p isolated from tunicamycin treated cells (FIG. 5; compare lanes 2 and 4). In addition, deletion of the carboxy-terminal 462 amino acid residues (the putative cytosolic domain) generated a protein that contained an N-linked oligosaccharide (data not shown). These results support localization of hIre1p to the ER which is consistent with the predicted topology of hIre1p having its amino termini in the ER lumen, similar to yeast Ire1p. Mori, K. et al., *Cell* 74:743-756 (1993).

Confocal laser scanning immunofluorescence microscopy was used to identify the hIre1p subcellular localization. COS-1 cells were transiently transfected with the wild-type hIRE1 expression plasmid and cells were double labeled with mouse antibody specific to hIre1p and rabbit antibody specific to GRP94, a resident protein of the ER. The immune complexes were visualized by secondary antibody conjugated with fluorescein isothiocyanate (FITC) or rhodamine, respectively (FIG. 6A). It was not possible to detect staining of hIre1p in non-transfected cells, possibly due to its low level of expression. In contrast, wild-type hIre1p was detected in transfected cells as perinuclear fluorescence and appeared similar to the fluorescence pattern observed for endogenous GRP94. Although the fluorescence patterns of the two proteins were similar, analysis of the merged images suggested that hIre1p was preferentially localized close to the nuclear membrane. Significantly greater staining was observed in cells transfected with the hIRE1 mutant K599A expression plasmid, consistent with its greater level of expression (FIG. 6B). The mutant hIre1p protein was also preferentially localized to the perinuclear region indicating that the kinase activity is not required for this localization. In order to determine if hIre1p was localized to the nuclear envelope, the fluorescence pattern of wild-type hIre1p was compared to that of endogenous RanGAP1 protein, a component of the nuclear pore complex. Mahajan, R. et al., *Cell* 88:97-107 (1997). Unlike hIre1p which was localized to the ER membrane throughout the cytoplasm, RanGAP1 protein exhibited a specific nuclear rim fluorescence staining pattern. Interestingly, when the two fluorescence images were merged, a sub-population of hIre1p indeed co-localized with the nuclear pore complex protein RanGAP1 (FIG. 6C).

Over-expression of kinase defective K599A hIre1p blocks the unfolded protein response in mammalian cells. The previous data demonstrate that hIre1p displays several features similar to those of *S. cerevisiae* Ire1p. To directly test whether hIre1p plays an essential role in the UPR in mammalian cells, a mammalian reporter plasmid was constructed by inserting a 0.5 kb fragment of the rat BiP promoter, including the cis-acting element capable of mediating the UPR (Chang, S. C. et al., *Proc. Natl. Acad. Sci. USA.* 84:680-684 (1987)), upstream from a luciferase coding region. The UPR reporter plasmid was co-transfected with either wild-type or the mutant K599A hIre1p expression vectors into COS-1 cells. The luciferase activity reflects the activation of the UPR in these cells. Luciferase activity was detected in extracts from cells transfected with the reporter plasmid alone and this activity was further increased 3-fold by treatment of the cells with tunicamycin (FIG. 7). Co-transfection of the reporter plasmid with pED-hIRE1 K599A prevented induction of the UPR upon tunicamycin (Tm) treatment. The inability to elicit the response suggests that the mutant hIre1p can act as a trans-dominant negative kinase to downregulate endogenous Ire1p. In contrast, over-expression of wild-type hIre1p caused constitutive induction of the UPR that was not further increased by treatment with tunicamycin. These results are consistent with those previously reported for expression of yeast Ire1p in *S. cerevisiae* (Mori, K. et al., *Cell* 74:743-756 (1993); Shamu, C. E. et al., *EMBO J.* 15:3028-3039 (1996)) and support the conclusion that hIre1p is a proximal sensor of the UPR pathway in mammalian cells.

II. Materials and Methods

Cloning of human IRE1 cDNA. A degenerate antisense oligonucleotide [5' (TC)TT (AG)CT IT(AG) ICC (AG)AA (AG)TC IG(AT) IAT 3'] (SEQ ID NO:7) was designed from the conserved amino acid sequence in kinase subdomain VII (ISDFGLCK, SEQ ID NO:8) between *S. cerevisiae* IRE1/ERN1 and its putative homologue from *C. elegans*. Inosine was incorporated into positions to minimize degeneracy and improve stability upon hybridization (Sambrook, J., Fritsch, E. F. and Maniatis, T. 1989. Molecular cloning: A laboratory manual (Cold Spring Harbor, N.Y.: Cold Spring Harbor Laboratory press)). This primer and a λgt 10 specific primer were used to amplify sequences from a human fetal liver cDNA library (Clontech). Total PCR products were ligated into the TA cloning vector (Invitrogen) and transformed into *E. coli* DH5α. A candidate clone, RH3, that showed highest homology to the yeast IRE1 and its counterpart gene in *C. elegans* was subsequently used to screen the λgt 10 human fetal liver cDNA library by standard procedures (Sambrook, J., Fritsch, E. F. and Maniatis, T. 1989. Molecular cloning: A laboratory manual (Cold Spring Harbor, N.Y.: Cold Spring Harbor Laboratory press)). The 5' end of the hIRE1 (F14) was obtained by 5' rapid amplification of cDNA ends (RACE) PCR (Bethesda Research Labs) using template RNA isolated from the human hepatoma cell line HepG2. Each cDNA fragment was subcloned into pBluescript II SK(−) plasmid (Stratagene) at the EcoR I site. All cDNA fragments were sequenced from both directions using the dideoxynucleotide sequencing method (Sequenase, Amersham).

pBluescript-13-1 is a recombinant plasmid containing the largest open reading frame of hIre1p but lacking the 5' end fragment. To assemble the full lengthhIRE1 cDNA, the 0.3 kb PCR product including the initiator methionine was amplified from pBluescript-F14 using two primers: 1058G (5' GCT CTA GAA CCA TGC CGG CCC GGC GGC T 3') (SEQ ID NO:9) and 865G (5' AGG CTG CCA TCA TTA GGA TCT 3') (SEQ ID NO:10) and Vent DNA polymerase (New England Biolabs). The 0.3 kb PCR product was introduced into clone 17-1 by overlap-extension PCR using two primers: 1058G and 9241B (5' CAT TGA TGT GCA TCA CCT TCC TC 3') (SEQ ID NO:11) to yield a 0.7 kb PCR product. The 0.7 kb fragment was digested with Xba I located upstream to the first ATG introduced by PCR, and BamH I. The fragment was ligated to pBluescript-17-1 at the same restriction endonuclease sites to yield pBluescript-17-1/5'. The 0.9 kb Xba I/Sac II fragment from pBluescript-17-1/5' was ligated to pBluescript-13-1 at the same sites to yield pBluescript-hIRE1. The 3.5 kb Xba I/EcoR I hIRE1 cDNA was subcloned into the XbaI site of the mammalian expression vector, pED (pEDΔC) (Kaufman, R. J. et al., *Nucl. Acids Res.* 19:4485-4490 (1991)) to yield pED-hIRE1.

Site directed mutagenesis. The conserved lysine residue at position 599 in kinase subdomain II was mutated by a PCR-based method using Vent DNA polymerase (New England Biolabs). The Mst I and Pvu I fragment from pED-hIRE1 was replaced with the homologous fragment containing mutated sequence (AAG→GCG) to yield pED-hIRE1 K599A. The mutation was confirmed by DNA sequencing.

Antibody production. The 1.6 kb cDNA encoding the entire cytoplasmic domain of hIre1p (amino acid residues 460 to 977) was generated by PCR amplification using primer 168G (5' CGG AAT TCA TCA CCT ATC CCC TGA GCA TG 3') (SEQ ID NO:12), 169G (5' CGG AAT TCT CAG AGG GCG TCT GGA GTC A 3') (SEQ ID NO:13) and Vent DNA polymerase (New England Biolabs). In order to make GST-hIre1p fusion protein, the PCR product was inserted in frame into pGEX-1λT (Pharmacia) at the EcoR I site and then transformed into *Escherichia coli* DH5α. The fusion protein was produced and purified as described by Frangioni and Neel (*Cell* 57:1069-1072 (1993)) except that the induction was performed at 30° C. The purified GST-cytoplasmic hIre1p fusion protein was repeatedly injected into mice as described by Harlow and Lane (1988). Sera collected from tail bleed was used for determining the titer by Western blot analysis. When optimal titer was obtained, the mice were injected with the sarcoma cell line S180 to induce ascites fluid that was directly used. Harlow, E. and Lane, D. 1988. Antibodies: A laboratory manual (Cold Spring Harbor, N.Y.: Cold Spring Harbor Laboratory press).

Transient DNA transfection and analysis. COS-1 monkey cells were transfected as previously described. Kaufman, R. J., *Methods Mol. Biol.* 62:287-300 (1997). Briefly, cells were plated the day before transfection. Cells were transfected with 2 μg/ml of pED-hIRE1 or pED-hIRE1 K599A plasmid DNA by the diethylaminoethyl-dextran method for 6 hr. The cells were fed with fresh media at 36 hr post-transfection. Total cell extract was prepared from the transfected cells at 60 hr post-transfection by using Nonidet P-40 lysis buffer (1% NP-40, 50 mM Tris-HCl, pH 7.5, 150 mM NaCl, 0.05% SDS) supplemented with 1 mM phenylmethylsulfonylfluoride, 40 μg/ml aprotinin, and 20 μg/ml leupeptin. For metabolic labeling (unless otherwise specified), the transfected cells were labeled with [$^{35}$S]-methionine and cysteine (1000 Ci/mmole, Amersham Corp.) for 15 min before harvesting cells. For immunoprecipitation, cell extract was preabsorbed with protein A sepharose. The precleared lysate was subsequently incubated with α-hIre1p for 14 hr at 4° C. and then incubated with rabbit α-mouse IgG antibodies for 1 hr. The immune complexes were adsorbed with protein A sepharose and successively washed with phosphate buffered saline (PBS) containing Triton X-100 at 1%, 0.1% and 0.05%. Samples were analyzed by SDS-PAGE under reducing conditions and autoradiography. Band intensities were quantified using the NIH Image 1.55b program.

Northern Blot analysis. Poly (A)$^+$ RNA isolated from various human tissues (Clontech) was hybridized with $^{32}$P-labeled-1.5 kb Nsi I/Pvu I fragment of hIRE1 cDNA corresponding to the luminal domain of hIre1p, the 0.9 kb EcoR I insert fragment of pBluescript-9-1 corresponding to the cytoplasmic domain of hIre1p, or 2 kb human β-actin cDNA (Clontech). The hybridization was performed in ExpressHyb Hybridization buffer according to the manufacturer's instructions (Clontech).

Total RNA from transfected COS-1 cells were prepared by using TRIzol reagent (Bethesda Research Labs). RNA (10 μg) was resolved in 1% formaldehyde agarose gel and blotted onto Hybond nylon membrane (Amersham). Blot were hybridized with $^{32}$P labeled 0.9 kb EcoR I fragment of hIRE-1 pBluescript-9-1 as described. Sambrook, J., Fritsch, E. F. and Maniatis, T. 1989. Molecular cloning: A laboratory manual (Cold Spring Harbor, N.Y.: Cold Spring Harbor Laboratory press).

In vitro phosphorylation and western blotting. Immunoprecipitated protein from transfected COS-1 cells was incubated in kinase buffer {50 mM Tris-HCl pH 7.4, 150 mM NaCl, 1 mM MnCl$_2$, 1 mM MgCl$_2$, 1 mM Na$_2$MoO$_4$, 2 mM NaF, 1 mM dithiothreitol and 10 μCi [γ-$^{32}$P]-ATP (6000 Ci/mmole, Amersham Corp.)} at 30° C. for 40 min. The protein samples were resolved by electrophoresis on an SDS-10% polyacrylamide gel and then transferred onto a nitrocellulose membrane. The membrane was probed with mouse α-hIre1p antibody followed with goat α-mouse antibody conjugated with alkaline phosphatase. The phosphorylation was quantified by autoradiography.

Confocal immunofluorescence microscopy. Immunofluorescence staining was followed as described by Paterson et al. *Meth. Enzymol* 256:162-173 (1995). Briefly, COS-1 cells were plated onto coverslips and transfected with pED-hIRE1 plasmid as described above. At 60 hr post-transfection, the transfected cells were stained with mouse α-GST-hIre1p and either rabbit α-GRP94 or guinea pig α-RanGAP1. The cells were then incubated with secondary antibodies (goat α-mouse IgG conjugated with fluorescein isothiocyanate and goat α-rabbit or goat α-guinea pig conjugated with rhodamine) (Boehringer Mannheim), washed, and mounted onto slides with Prolong mounting (Molecular Probes). The fluorescence images were examined using a confocal laser scanning fluorescence microscope (Bio-Rad MRC 600).

In vitro cleavage of HAC1 mRNA. The procedure followed was previously described by Sidrauski and Walter, *Cell* 90:1031-1039 (1997). Briefly, a 550 bp fragment of HAC1 DNA fragment flanking the intron region (Mori, K. et al., *Genes to Cells*. 1:803-817 (1996)) was PCR amplified from *S. cerevisiae* genomic DNA and subcloned into pBluescript II SK (−) plasmid (Stratagene) at Pst I and Xho I sites (pBluescript-HAC1 ). HAC1 mRNA was transcribed in vitro from Xho I digested pBluescript-HAC1 using T7 RNA polymerase (Boehringer Mannheim) in the presence of $\alpha^{32}$P-UTP (3000 Ci/mmole, Amersham Corp.). The RNA was resolved by electrophoresis in a 5% denaturing polyacrylamide gel and the $^{32}$P-labeled HAC1 mRNA was purified as described (Sidrauski, K. et al., *Cell* 90:1031-1039 (1997)) and dissolved in endonuclease buffer (20 mM Hepes, 1 mM DTT, 10 mM MgOAc, 50 mM KOAc, 2 mM ATP). Purified RNA (3×10 cpm) was added to the immunoprecipitated hIre1p, hIre1p K599A, or 0.5 µg GST-cytoplasmic Ire1p (Welihinda, A. A. et al., *J. Biol. Chem*. 271:18181-18187 (1995)) in final volume 100 µl reaction. After incubating at 30° C. for the indicated time, the reaction was terminated by extraction with phenol/chloroform, precipitated with ethanol, and analyzed by electrophoresis on are 5% denaturing polyacrylamide gel. Gels were dried prior to autoradiography.

Primer extension. The procedure was followed as described by Sambrook et al., Molecular cloning: A laboratory manual (Cold Spring Harbor, N.Y.: Cold Spring Harbor Laboratory press) (1989).

Luciferase assay. To construct the pBiP-luciferase reporter plasmid, the promoter region of rat BiP gene including the putative unfolded protein response element (nt −457 to +33; Chang, S. C. et al., *Proc. Natl. Acad. Sci. USA* 84:680-684 (1987)) was amplified by PCR and subcloned into the Kpn I and Hind III sites of pGL3-basic vector (Promega). Each 10 cm plate of COS-1 cells was co-transfected with pBiP-luciferase reporter plasmid (2 µg), RSVβ-gal (2 µg) and pED-hIRE1 or pED-hIRE1-K599A (4 µg each) by the calcium phosphate procedure. Chen, C. A. et al., *BioTechniques* 6:632-638 (1988). At 60 hr post-transfection, cells were treated with or without 10 µg/ml tunicamycin for 6 hr. Preparation of the cell lysate β-galactosidase assays and luciferase assays were performed according to manufacturer's instructions (Promega). The luciferase activity was normalized to β-galactosidase activity.

III. Discussion hIre1p has an intrinsic autophosphorylation and endoribonuclease activity. Previous studies on the yeast Ire1p demonstrated that the endoribonuclease activity required an adenine nucleotide as a cofactor. Since, a nonhydrolyzable analogue AMP-PNP and ADP stimulated the activity as well as ATP, it was thought that the endoribonuclease activity of yeast Ire1p did not require the kinase activity. As demonstrated in the present invention, the mutant K599A hIre1p had defective kinase activity as well as endoribonuclease activity, suggesting that autophosphorylation is required to elicit the endoribonuclease activity, possibly by phosphorylation of residues within its endoribonuclease domain. The studies presented herein suggest that the hIre1p endoribonuclease activity requires autophosphorylation as well as an adenine nucleotide. However, the K599A mutant Ire1p may be defective in endoribonuclease activity as a consequence of altered nucleotide binding, and not necessarily due to a requirement for autophosphorylation. hIre1p was able to cleave the yeast HAC1 mRNA substrate at the identical 5' splice site as yeast Ire1p. However, primer extension analysis identified the 5' cleavage site was after guanine 661, in contrast to previous primer extension analysis that identified cytosine 660 as the 5' cleavage site (Sidrauski and Walter 1997), but consistent with the recent characterization of in vivo spliced products derived from mutated templates (Kawahara et al. 1998). Whereas the primer extension analysis of the present invention was compared to a DNA sequencing ladder derived from a reaction using the same primer for extension, Sidrauski and Walter (*Cell* 90:1031-1039 (1997)) used a different primer and this may explain the discrepancy. Although hIre1p efficiently cleaved the 5' splice site of yeast HAC1 mRNA, there was no detectable cleavage at the 3' splice site. This is consistent with observations that hIre1p was not able to complement *S. cerevisiae* deleted of IRE1. The complete cleavage of HAC1 mRNA at both splice sites is required for the UPR function in yeast. Sidrauski, K. et al., *Cell* 90:1031-1039 (1997); Kawahara, T. et al, *J. Biol. Chem*. 273:1802-1807 (1998). The inability for hIre1p to cleave the yeast HAC1 mRNA 3' splice site was surprising since Kawahara et al. (*J. Biol. Chem*. 273:1802-1807 (1998)) recently demonstrated that the sequence requirements for the 5' and 3' splice site cleavages within HAC1 mRNA by yeast Ire1p are remarkably similar. However, there were a couple nucleotide differences in cleavage specificity identified between the 5' and 3' splice sites, particularly the +1 position and the +5 position with respect to the site of cleavage. Therefore, the hIre1p cleavage specificity for the 3' splice site may have diverged from the yeast Ire1p. Alternatively, there may be another homologue of hIre1p that displays a different cleavage specificity restricted to the 3' splice site of a human HAC1 mRNA homologue, and the two nucleolytic events required to release the intron may require a heterodimer, of which each subunit has unique specificity to catalyze cleavage at either the 5' or 3' splice site. This latter possibility is observed in the cleavage specificity of yeast tRNA endonuclease, where two subunits are required, each having its own active site that recognizes either the 5' or 3' splice site of precursor tRNA molecules. Trotta, C. R. et al., *Cell* 89:849-858 (1997).

Expression of wild-type hIre1p was approximately 16-fold reduced compared to K599A catalytically inactive mutant hIre1p. The reduced expression of the wild-type kinase was not due to a general toxicity or transcriptional inhibition specific to the promoter used in the expression vector since expression of a co-transfected cDNA, eIF-2α, contained within the same expression vector was not reduced in the presence of the wild-type hIre1p kinase expression vector. Analysis of mRNA demonstrated that the wild-type kinase also had a corresponding decrease in the steady state level of mRNA compared to the mRNA encoding the K599A mutant Ire1p. Since the K599A mutant hIRE1 mRNA had only 2 base changes compared to the wild-type hIRE1 mRNA, it is expected that the reduced steady state level of hIRE1 mRNA is a consequence of activated hIre1p kinase activity. It is possible that the expression of wild-type Ire1p is limited due to a specific autoregulatory process in which the endoribonuclease activity of activated Ire1p cleaves its own mRNA, resulting in its degradation. The specific feedback on hIRE1mRNA suggests that the biosynthesis of hIre1p is tightly controlled. Stringent regulation of Ire1p synthesis may be necessary for cell survival as overproduction of Ire1p leads to constant activation of the UPR pathway and retardation of cell growth. Shamu, C. E. , et al., *EMBO J*. 15:3028-3039 (1996).

Although the extremely low levels of endogenous Ire1p precluded its direct visualization in mammalian cells, overexpressed wild-type Ire1p was preferentially localized to a subcompartment within the ER, with particular concentration around the nuclear envelope. In addition, a portion of hIre1p was colocalized with RanGAP1, a protein associated with the nuclear pore complex suggesting that hIre1p might be a component of the nuclear pore complex. This localization would be ideal if hIre1p-dependent RNA splicing is coupled with nucleo-cytoplasmic transport of substrate RNA molecules. In S. cerevisiae, the tRNA ligase, Rlg1p, mediates ligation of the HAC1mRNA cleaved substrate (Sidrauski, K. et al., Cell 90:1031-1039 (1997)) and is also localized to the nucleoplasmic side of the nuclear pore. Simos, G. et al., EMBO J. 15:2270-2284 (1996).

The remarkable conservation between yeast Ire1p and hIre1p functional activities suggests the existence of a human homologue to yeast HAC1 that may exhibit selective mRNA cleavage and ligation by a human homologue of S. cerevisiae tRNA ligase gene RLG1. Furthermore, additional components of this pathway may also be conserved. For example, in S. cerevisiae the transcriptional co-activator complex having histone acetyltransferase activity composed of Gcn5p, Ada2p, and Ada3p is required for maximal transcriptional induction of the KAR2 promoter. Welihinda, A. A. et al., Proc. Nati. Acad. Sci. USA. 94:4289-4294 (1997). In addition, Ada5p, another component of this complex, is absolutely required to elicit the UPR. Welihinda, A. A. et al., Proc. Nati. Acad. Sci. USA 94:4289-4294 (1997). An interaction between Gcn5p and Ire1p was demonstrated (Welihinda, A. A. et al., Proc. Nati. Acad. Sci. USA 94:4289-4294 (1997)) and suggests that the nucleoplasmic domain of Ire1p, localized to the nuclear envelope, may serve as a nucleation site for assembly of a multisubunit transcriptional activator complex required for transcriptional activation of genes under control of the UPRE. Human homologues for several of these transcriptional co-activator gene products have been identified (Candau, R. et al., Mol. Cell. Biol. 16:593-602 (1996)), and it is likely that these products also participate in transcriptional activation of the ER-stress responsive genes in higher eukaryotes. In addition, a Ser/Thr protein phosphatase of the PP2C gene family that is required to turn off activated Ire1p signaling in response to unfolded protein has recently been described. Welihinda, A. A. et al., Mol. Cell. Biol. In press (1998).

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All patents and other publications cited herein are expressly incorporated by reference.

We claim:

1. An isolated nucleic acid molecule encoding hIre1p comprising the nucleotide sequence of SEQ ID NO:1.

2. A vector comprising the nucleic acid molecule of claim 1.

3. An isolated host cell transfonned with the nucleic acid molecule of claim 1.

4. The cell of claim 3, wherein the cell is a mammalian cell.

5. The cell of claim 3, wherein the cell is a bacterial cell.

6. An isolated transfected cell producing the protein encoded by the nucleic acid molecule of claim 1.

7. An isolated host cell transformed with the vector of claim 2, wherein the polynucleotide is operably linked to vector expression sequences.

8. The host cell of claim 7, wherein said cell is a mammalian cell.

9. The host cell of claim 7, wherein the cell is a bacterial cell.

* * * * *